United States Patent
Van Wyk

(10) Patent No.: US 8,992,521 B2
(45) Date of Patent: *Mar. 31, 2015

(54) FLEXIBLE ELECTROSURGICAL ABLATION AND ASPIRATION ELECTRODE WITH BEVELED ACTIVE SURFACE

(71) Applicant: ElectroMedical Associates, LLC, Bethesda, MD (US)

(72) Inventor: Robert A. Van Wyk, St. Pete Beach, FL (US)

(73) Assignee: ElectroMedical Associates, LLC, Bethesda, MD (US)

( * ) Notice: Subject to any disclaimer, the term of this patent is extended or adjusted under 35 U.S.C. 154(b) by 165 days.

This patent is subject to a terminal disclaimer.

(21) Appl. No.: 13/659,175

(22) Filed: Oct. 24, 2012

(65) Prior Publication Data

US 2013/0053842 A1     Feb. 28, 2013

Related U.S. Application Data

(63) Continuation-in-part of application No. 13/091,584, filed on Apr. 21, 2011.

(60) Provisional application No. 61/342,990, filed on Apr. 22, 2010.

(51) Int. Cl.
    *A61B 18/14*     (2006.01)
    *A61B 18/00*     (2006.01)
    *A61B 19/00*     (2006.01)

(52) U.S. Cl.
    CPC ..... *A61B 18/148* (2013.01); *A61B 2018/00107* (2013.01); *A61B 2018/00577* (2013.01); *A61B 2019/4018* (2013.01); *A61B 2218/001* (2013.01);

(Continued)

(58) Field of Classification Search
CPC .. A61B 18/148; A61B 18/1482; A61B 18/14; A61B 18/00577; A61B 2018/00589; A61B 2018/100595; A61B 2018/00607; A61B 2018/00964; A61B 2018/00315; A61B 2018/00571; A61B 2018/1405; A61B 2018/1497; A61B 2018/00625
USPC ...................................................... 606/41–49
See application file for complete search history.

(56) References Cited

U.S. PATENT DOCUMENTS

| 2,448,741 A | 9/1948 | Scott et al. |
| 3,856,015 A | 12/1974 | Iglesias |
| 3,901,242 A | 8/1975 | Storz |

(Continued)

*Primary Examiner* — Joseph Stoklosa
*Assistant Examiner* — Eunhwa Kim
(74) *Attorney, Agent, or Firm* — Chalin A. Smith; Smith Patent

(57) ABSTRACT

Disclosed herein is a flexible single piece active element for use in connection with aspirating electrosurgical ablators, particularly those configured for bulk tissue vaporization. The active electrode elements of the present invention provide a simple construction suitable for use with a wide array of electrosurgical components and adjustable to wide range of angled positions to permit access to a variety of tissues, in an array of diverse environments and address a host of ablation needs. Additionally, the novel geometry and positioning of both ablation surface and aspiration ports permit aspiration flow to remove primarily waste heat rather than process heat, to thereby improve vaporization efficiency and reduce procedure time. Thus, active electrodes and ablation devices of the present invention maximize efficiency and adaptability while minimizing manufacturing cost and device profile.

20 Claims, 24 Drawing Sheets

(52) U.S. Cl.
CPC ............... *A61B 2018/00565* (2013.01); *A61B 2018/00625* (2013.01); *A61B 2218/008* (2013.01)
USPC .......................................................... 606/41

(56) References Cited

U.S. PATENT DOCUMENTS

| | | | |
|---|---|---|---|
| 4,674,499 A | 6/1987 | Pao | |
| 4,682,596 A | 7/1987 | Bales | |
| 4,726,370 A | 2/1988 | Karasawa | |
| 4,832,048 A | 5/1989 | Cohen | |
| 4,917,082 A | 4/1990 | Grossi et al. | |
| 5,195,959 A | 3/1993 | Smith | |
| 5,261,905 A | 11/1993 | Doresey, III | |
| 5,277,696 A | 1/1994 | Hagen | |
| 5,314,459 A | 5/1994 | Swanson et al. | |
| 5,582,610 A | 12/1996 | Grossi et al. | |
| 5,647,840 A | 7/1997 | D'Amelio et al. | |
| 5,681,282 A | 10/1997 | Eggers et al. | |
| 5,697,536 A | 12/1997 | Eggers et al. | |
| 5,709,698 A | 1/1998 | Adams et al. | |
| 5,782,829 A | 7/1998 | Swiantek et al. | |
| 6,033,400 A | 3/2000 | Grossi et al. | |
| 6,066,134 A | 5/2000 | Eggers | |
| 6,113,597 A | 9/2000 | Eggers et al. | |
| 6,169,926 B1 | 1/2001 | Baker | |
| 6,197,025 B1 | 3/2001 | Grossi et al. | |
| 6,235,020 B1 | 5/2001 | Cheng et al. | |
| 6,277,114 B1 | 8/2001 | Bullivant et al. | |
| 6,296,638 B1 | 10/2001 | Davison et al. | |
| 6,379,350 B1 | 4/2002 | Sharkey et al. | |
| 6,379,351 B1 | 4/2002 | Thapliyal et al. | |
| 6,391,025 B1 | 5/2002 | Weinstein et al. | |
| 6,419,684 B1 | 7/2002 | Heisler et al. | |
| 6,468,274 B1 | 10/2002 | Alleyne et al. | |
| 6,514,248 B1 | 2/2003 | Eggers et al. | |
| 6,565,560 B1 | 5/2003 | Goble et al. | |
| 6,575,968 B1 | 6/2003 | Eggers et al. | |
| 6,582,423 B1 | 6/2003 | Thapliyal et al. | |
| 6,589,237 B2 | 7/2003 | Woloszko et al. | |
| 6,767,347 B2 | 7/2004 | Sharkey et al. | |
| 6,770,070 B1 | 8/2004 | Balbierz | |
| 6,796,982 B2 | 9/2004 | Carmel et al. | |
| 6,837,884 B2 | 1/2005 | Woloszko | |
| 6,840,937 B2 | 1/2005 | Van Wyk | |
| 6,899,712 B2 | 5/2005 | Moutafis et al. | |
| 6,920,883 B2 | 7/2005 | Bessette et al. | |
| 6,921,398 B2 | 7/2005 | Carmel et al. | |
| 6,921,399 B2 | 7/2005 | Carmel et al. | |
| 6,955,676 B2 | 10/2005 | Quick | |
| 7,066,936 B2 | 6/2006 | Ryan | |
| 7,150,748 B2 | 12/2006 | Ebbutt et al. | |
| 7,166,103 B2 | 1/2007 | Carmel et al. | |
| 7,566,333 B2 | 7/2009 | Van Wyk et al. | |
| 7,611,509 B2 | 11/2009 | Van Wyk | |
| 7,837,683 B2 | 11/2010 | Carmel et al. | |
| 2001/0001314 A1 | 5/2001 | Davison et al. | |
| 2002/0038122 A1 | 3/2002 | Peters et al. | |
| 2002/0052600 A1 | 5/2002 | Davison et al. | |
| 2002/0072745 A1 | 6/2002 | Truckai et al. | |
| 2002/0120261 A1 | 8/2002 | Morris et al. | |
| 2002/0133148 A1 | 9/2002 | Daniel et al. | |
| 2002/0133149 A1 | 9/2002 | Bessette | |
| 2003/0083655 A1* | 5/2003 | Van Wyk | 606/41 |
| 2003/0088243 A1 | 5/2003 | Carmel et al. | |
| 2003/0120269 A1 | 6/2003 | Bessette et al. | |
| 2004/0006336 A1 | 1/2004 | Swanson | |
| 2004/0006339 A1 | 1/2004 | Underwood et al. | |
| 2004/0030330 A1 | 2/2004 | Brassel et al. | |
| 2004/0049183 A1 | 3/2004 | Ellman et al. | |
| 2004/0104455 A1 | 6/2004 | Shimizu | |
| 2004/0106919 A1 | 6/2004 | Hood | |
| 2004/0193150 A1 | 9/2004 | Sharkey et al. | |
| 2004/0230190 A1 | 11/2004 | Dahla et al. | |
| 2005/0065510 A1* | 3/2005 | Carmel et al. | 606/41 |
| 2005/0234446 A1* | 10/2005 | Van Wyk et al. | 606/41 |
| 2005/0277915 A1 | 12/2005 | DeCesare et al. | |
| 2006/0122680 A1 | 6/2006 | Auth et al. | |
| 2006/0184165 A1 | 8/2006 | Webster et al. | |
| 2006/0224154 A1 | 10/2006 | Shadduck et al. | |
| 2006/0235377 A1 | 10/2006 | Earley et al. | |
| 2006/0259031 A1* | 11/2006 | Carmel et al. | 606/41 |
| 2006/0293653 A1* | 12/2006 | Van Wyk | 606/41 |
| 2007/0043348 A1* | 2/2007 | Sutter et al. | 606/41 |
| 2008/0077129 A1 | 3/2008 | Van Wyk et al. | |
| 2008/0208189 A1 | 8/2008 | Van Wyk et al. | |
| 2009/0069802 A1 | 3/2009 | Garito et al. | |

\* cited by examiner

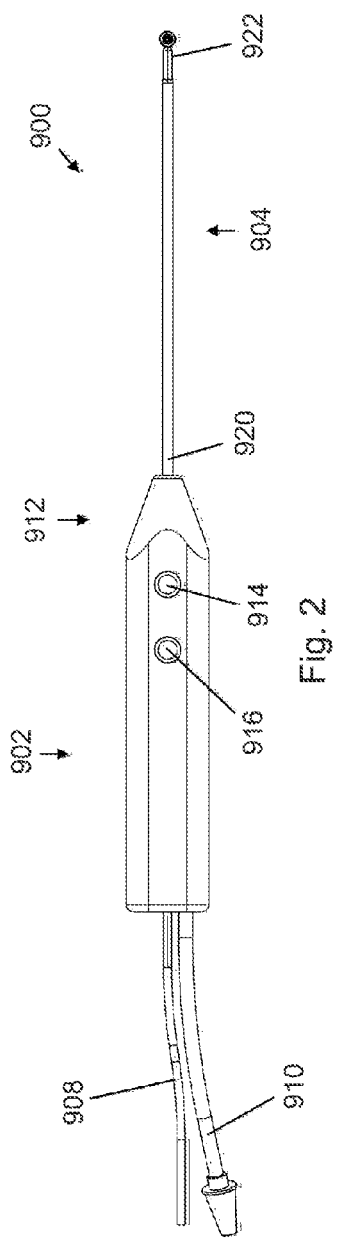
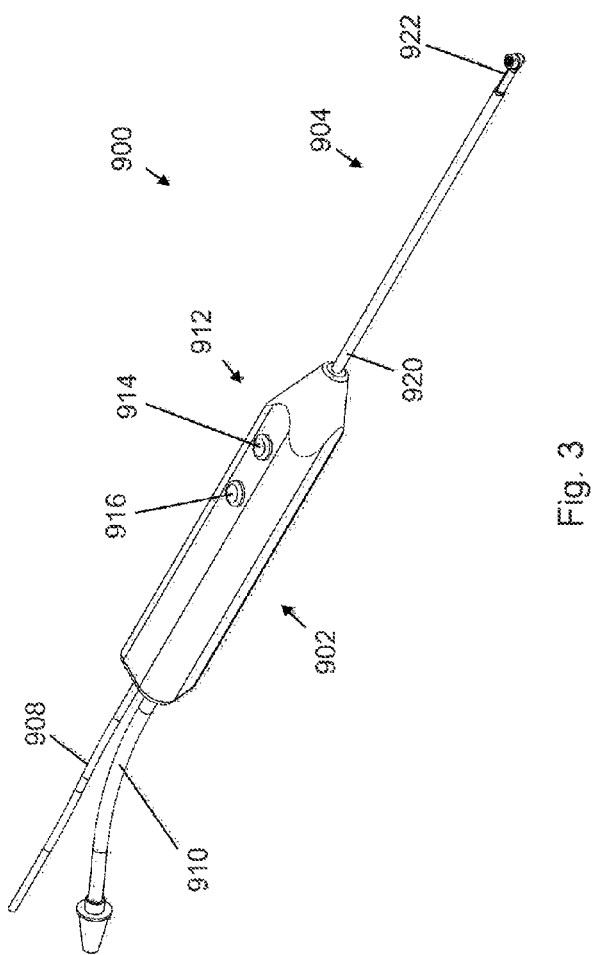

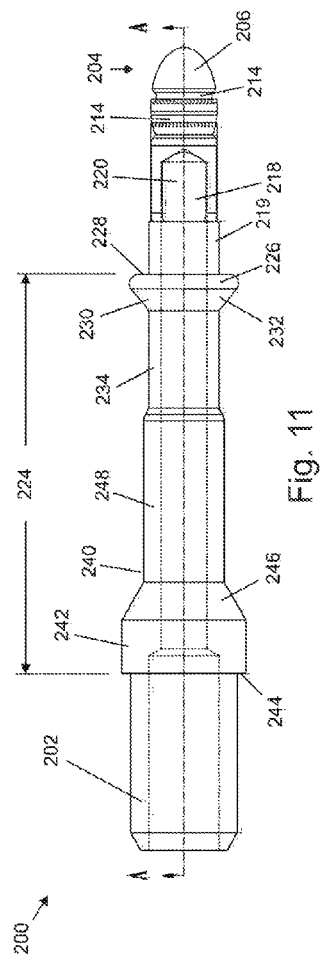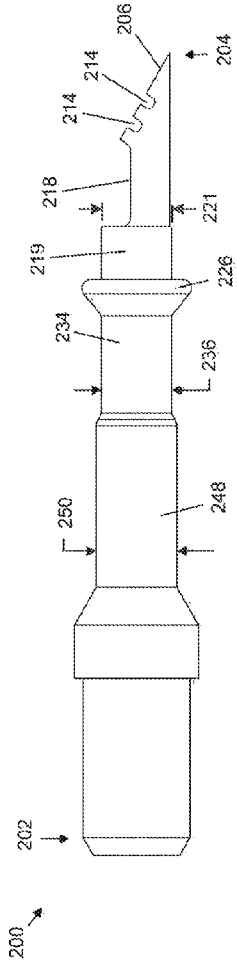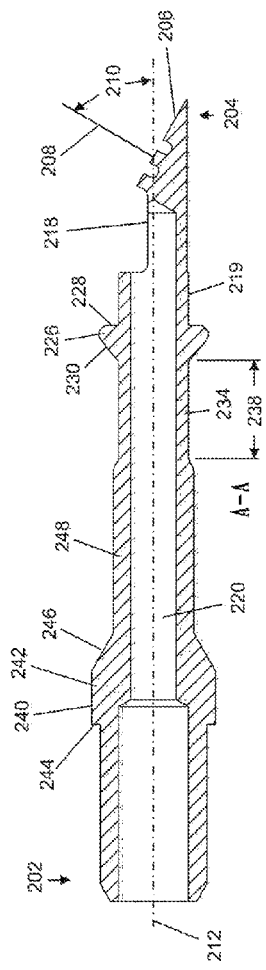

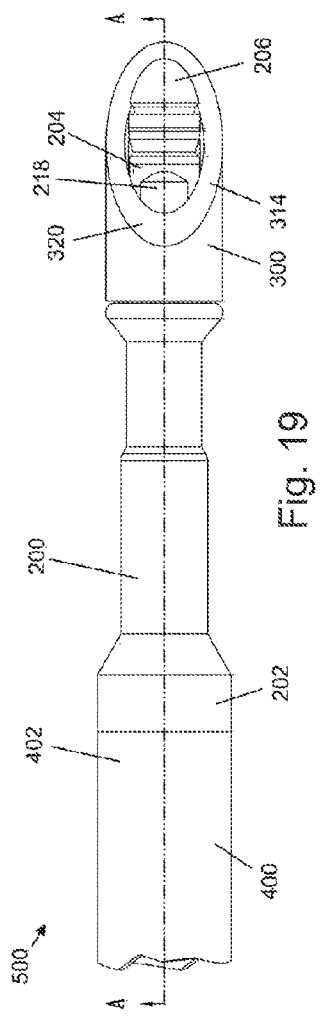
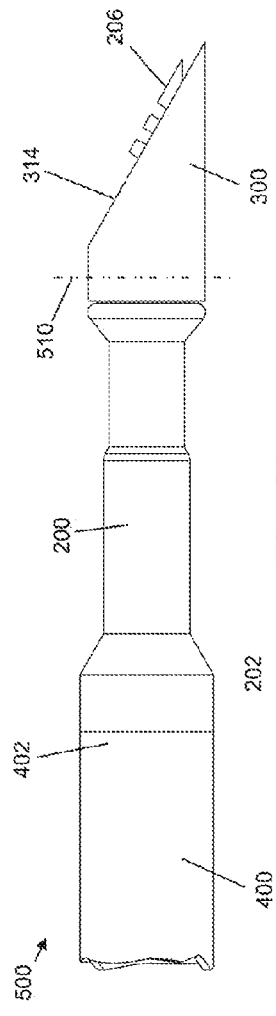
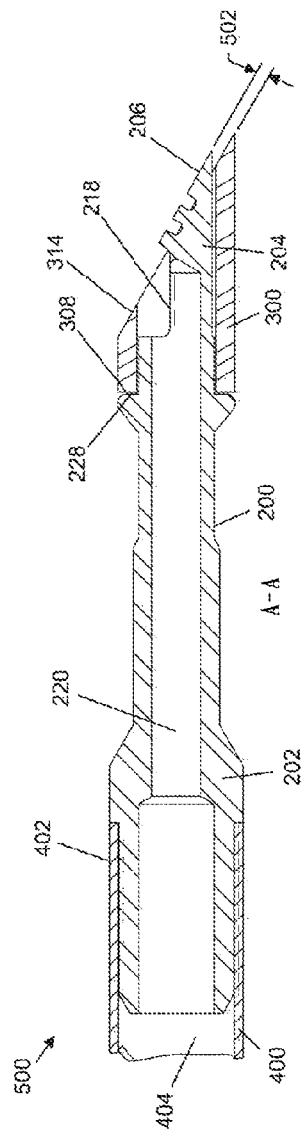
Fig. 19
Fig. 20
Fig. 21

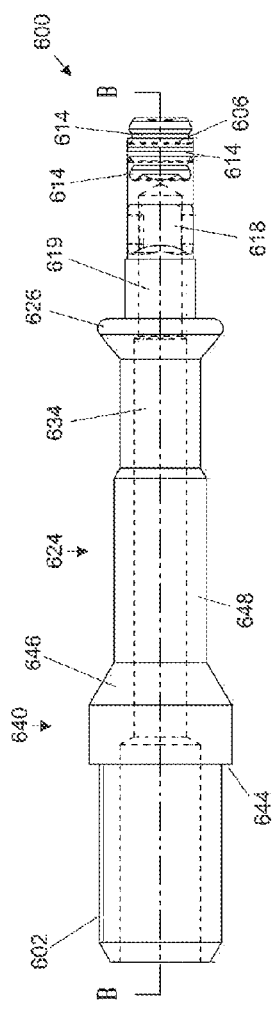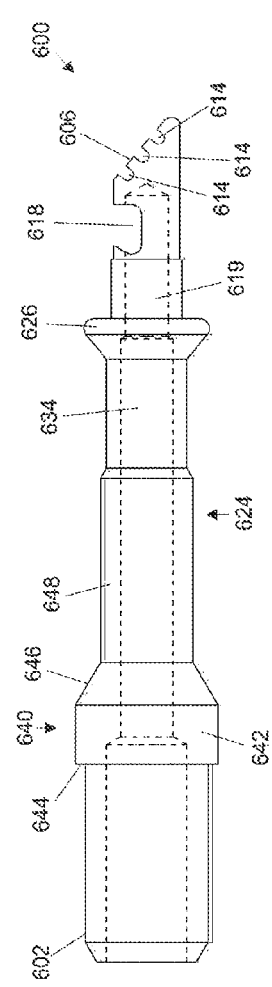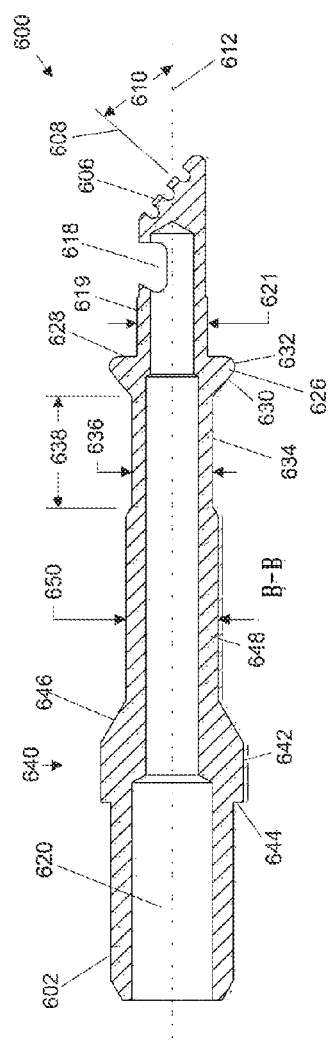

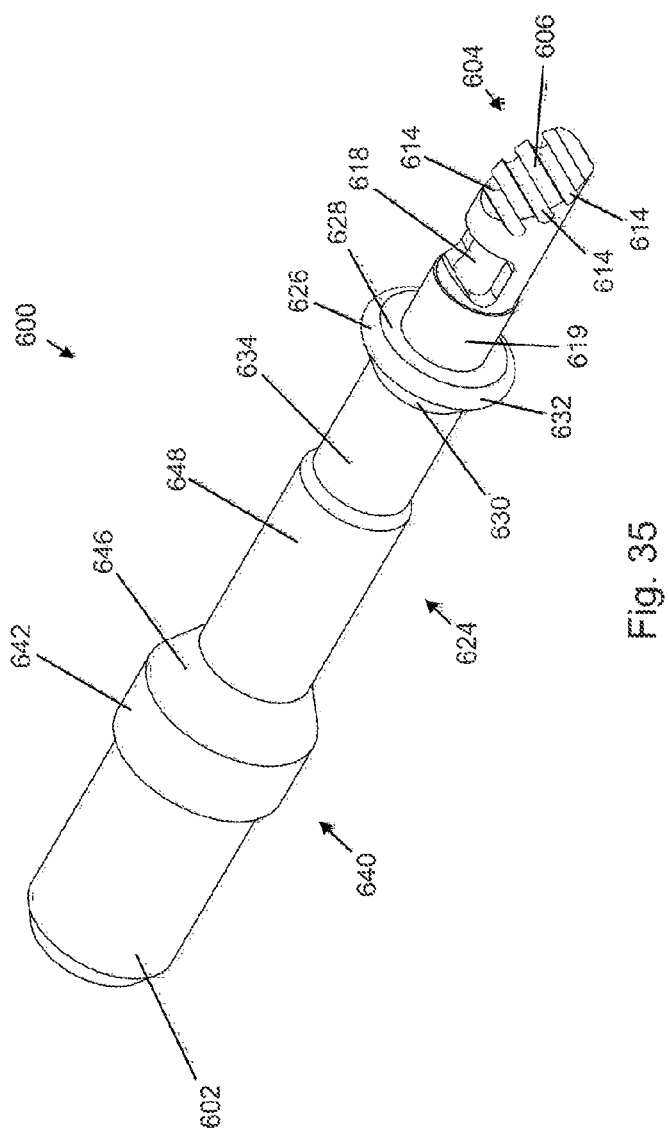
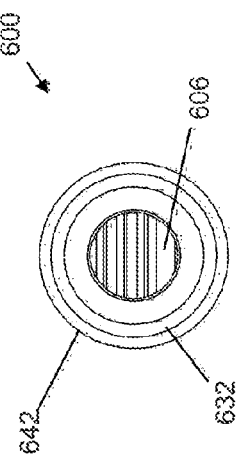
Fig. 35
Fig. 34

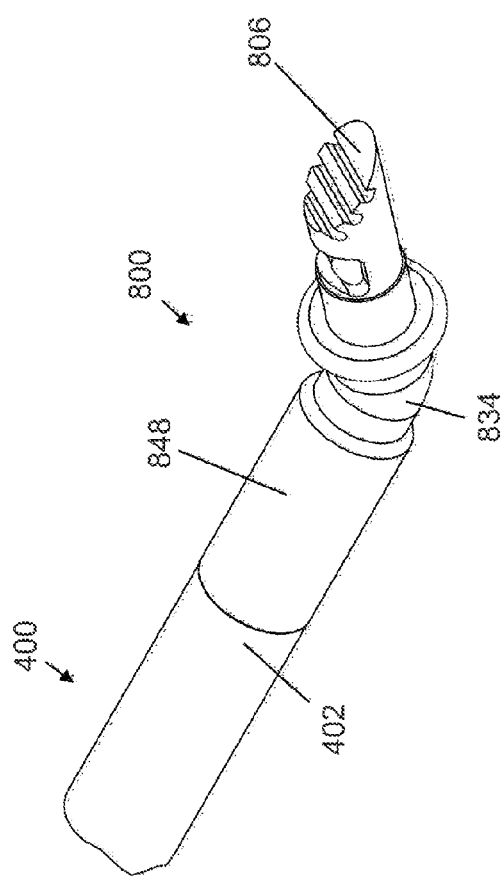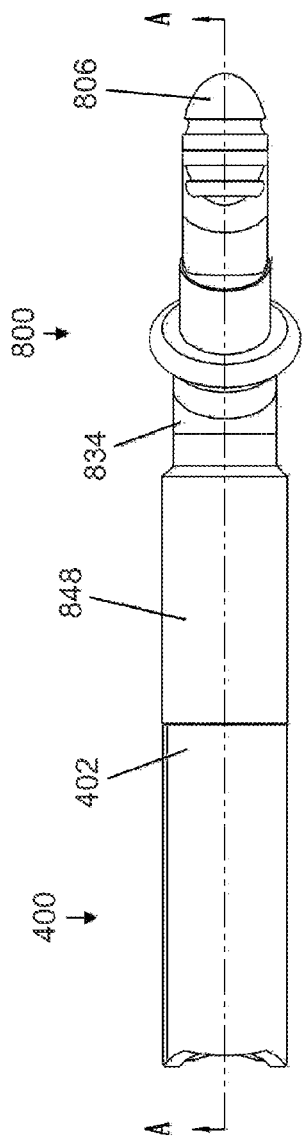

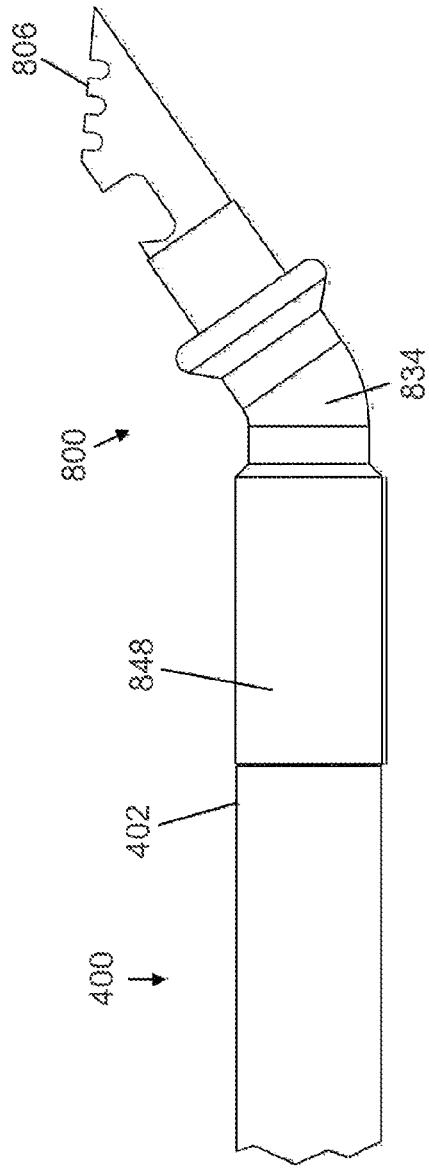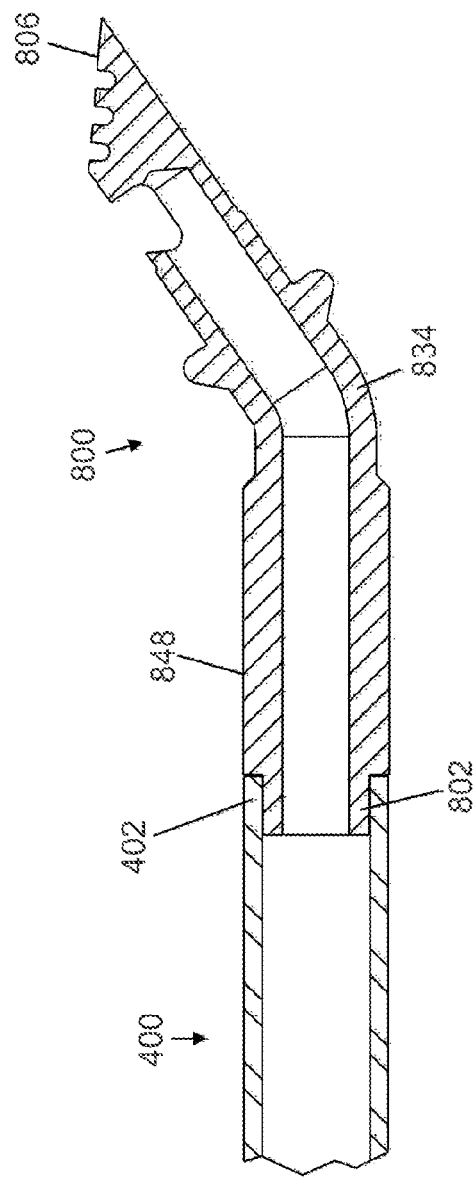

FLEXIBLE ELECTROSURGICAL ABLATION AND ASPIRATION ELECTRODE WITH BEVELED ACTIVE SURFACE

PRIORITY

This application is a continuation-in-part of U.S. patent application Ser. No. 13/091,584, filed Apr. 21, 2011, which, in turn, claims the benefit of U.S. Provisional Application Ser. No. 61/342,990, filed Apr. 22, 2010. The contents of all prior applications are hereby incorporated by reference herein in their entirety.

FIELD OF THE INVENTION

This invention relates to electrosurgical devices for use in a conductive fluid environment, and more specifically to aspirating ablation electrosurgical devices for bulk vaporization of tissue in a conductive fluid environment that may be manufactured at low cost and have increased efficiency through the minimization of process heat loss.

BACKGROUND OF THE INVENTION

Minimally invasive surgical techniques have gained significant popularity due to their ability to accomplish desirable outcomes with reduced patient pain and accelerated recovery and return of the patient to normal activities. Arthroscopic surgery, wherein the intra-articular space is filled with fluid, allows orthopedic surgeons to efficiently perform procedures using special purpose instruments designed specifically for arthroscopy. Among these special purpose tools are various manual graspers and biters, powered shaver blades and burs, and electrosurgical devices. During the last several years specialized arthroscopic electrosurgical electrodes referred to in the art as "ablators" have been developed. Examples of such instruments include ArthroWands manufactured by Arthrocare (Sunnyvale, Calif.), VAPR electrodes manufactured by Mitek Products Division of Johnson & Johnson (Westwood, Mass.) and electrodes by Smith and Nephew, Inc. (Andover, Mass.). These ablator electrodes differ from conventional arthroscopic electrosurgical electrodes in that they are designed for the bulk removal of tissue by vaporization rather than the cutting of tissue or coagulation of bleeding vessels. While standard electrodes are capable of ablation, their geometries are generally not efficient for accomplishing this task. The tissue removal rates of ablator electrodes are lower than those of arthroscopic shaver blades, however, electrosurgical ablators are used because they achieve hemostasis (stop bleeding) during use and are able to efficiently remove tissue from bony surfaces. Ablator electrodes are used in an environment filled with electrically conductive fluid.

During ablation, current flows from the ablator into the conductive fluid and heats the fluid to its boiling point. Heating of the conductive fluid is proportional to the density of electrical current flowing from the electrode into the fluid. Regions of high current density will experience higher rates of heating as compared to regions of low current density. In general, regions of high current density occur at the corners and edges of the electrode. Steam bubbles form first at the edges of an ablator but eventually cover virtually the electrode's entire surface. When a steam bubble reaches a critical size, arcing occurs within the bubble and enclosed portion of tissue. A train of sparks occurs within the bubble with the train ending when the bubble grows too large or the tissue enclosed in the bubble is evaporated and conditions within the bubble become unfavorable for sparking.

During ablation, water within the target tissue is vaporized. Because volumes of tissue are vaporized rather than discretely cut out and removed from the surgical site, the power requirements of ablator electrodes are generally higher than those of other arthroscopic electrosurgical electrodes. The efficiency of the electrode design and the characteristics of the Radio Frequency (RF) power supplied to the electrode also affect the amount of power required for ablation. Electrodes with inefficient designs and/or powered by RF energy with poorly suited characteristics will require higher power levels than those with efficient designs and appropriate generators. Because of these factors the ablation power levels of devices produced by different manufacturers vary widely, with some using power levels significantly higher than those commonly used by arthroscopists. Ablator electrode systems from some manufacturers may use up to 280 Watts, significantly higher than the 30 to 70 Watt range generally used by other arthroscopic electrosurgical electrodes.

During arthroscopic electrosurgery, all of the RF energy supplied to the electrode is converted into heat, thereby raising the temperature of the fluid within the joint and the temperature of adjacent tissue. Prior to the introduction of ablator electrodes, the temperature of the fluid within the joint was not of concern to the surgeon. However, due to the higher power levels at which they generally operate and the longer periods of time that they are energized, fluid temperature is a major concern during the use of ablator electrodes. Standard arthroscopic electrosurgical electrodes are usually energized for only brief periods, generally measured in seconds, while specific tissue is resected or modified, or a bleeder coagulated. In contrast, ablator electrodes are energized for longer periods of time, often measured in minutes, while volumes of tissue are vaporized.

The temperature of the fluid within the joint is critical since cell death occurs at 45.degree. C., a temperature easily reached with high-powered ablators if fluid flow through the surgical site is insufficient. Patient injury may result. Such injuries have been documented.

The likelihood of thermal injury is strongly affected by the amount of power supplied to the ablator. This, in turn, is determined by the efficiency of the ablator and the speed with which the surgeon desires to remove tissue. A highly efficient ablator will allow the surgeon to remove tissue at desirably high rates while requiring low levels of power. Under these conditions, the likelihood of thermal injuries is reduced significantly.

Ablator electrodes are produced in a variety of sizes and configurations to suit a variety of procedures. Ablators for use in ankle, wrist or elbow arthroscopy, for instance, are smaller than those used in the knee or shoulder. In each of these sizes, a variety of configurations are produced to facilitate access to various structures within the joint being treated. These configurations differ in the working length of the electrode (the maximum distance that an electrode can be inserted into a joint), in the size and shape of their ablating surfaces and in the angle between the ablating face and the axis of the electrode shaft. Electrodes are typically designated by the angle between a normal to the ablating surface and the axis of the electrode shaft, and by the size of their ablating surface and any associated insulator.

Primary considerations of surgeons when choosing a particular configuration of ablator for a specific procedure are its convenience of use (the ease with which the instrument is able to access certain structures) and the speed with which the ablator will be able to complete the required tasks. When choosing between two configurations capable of accomplishing a particular task, surgeons will generally choose the ablator with the larger ablating surface so as to remove tissue more quickly. This is particularly true for procedures during which large volumes of tissue must be removed. One such procedure is acromioplasty, the reshaping of the acromion. The underside of the acromion is covered with highly vascular tissue that may bleed profusely when removed by a conventional powered cutting instrument, such as an arthroscopic shaver blade. Ablator electrodes are used extensively during this procedure since they are able to remove tissue without the bleeding which obscures the surgeon's view of the site. Ablation in the area under the acromion is most efficiently accomplished using an electrode on which a line normal to the ablating surface is approximately perpendicular to the axis of the ablator shaft. Such an electrode is designated as a "90 Degree Ablator" or a "side effect" ablator. Examples of such electrodes include the "3.2 mm 90 Degree Three-Rib UltrAblator" by Linvatec Corporation (Largo, Fla.), the "90 Degree Ablator" and "90 Degree High Profile Ablator" by Smith and Nephew (Andover, Mass.), the "Side Effect VAPR Electrode" by Mitek Products Division of Johnson and Johnson, and the "3.5 mm 90 Degree Arthrowand", "3.6 mm 90 Degree Lo Pro Arthrowand", and "4.5 mm 90 Deg. Eliminator Arthrowand" by Arthrocare Corporation.

Recently ablator electrodes have been configured with a means of aspiration to remove bubbles and debris from the surgical site. During electrosurgery in a conductive fluid environment, tissue is vaporized, thereby producing steam bubbles that may obscure the view of the surgeon or displace saline from the area of the intra-articular space that the surgeon wishes to affect. In the case of ablation (bulk vaporization of tissue), the number and volume of bubbles produced is even greater than when using other electrodes since fluid is continually boiling at the active electrode during use. Ideally, flow through the joint carries these bubbles away; however, in certain procedures this flow is insufficient to remove all of the bubbles. The aspiration means on an aspirating ablator removes some bubbles as they are formed by the ablation process, and others after they have collected in pockets within the joint. The ablator aspiration means is typically connected to an external vacuum source that provides suction for bubble evacuation.

Aspiration on currently available ablator products may be divided into two categories according to their level of flow. High-flow ablators have an aspiration tube, the axis of which is coaxial with the axis of the ablator rod or tube, that draws in bubbles and fluid through its distal opening and/or openings cut into the tube wall near its distal tip. High-flow ablators may decrease the average joint fluid temperature by removing heated saline (waste heat since it is an undesirable byproduct of the process) from the general area in which ablation is occurring. The effectiveness of the aspiration, both for removal of bubbles and for removal of waste heat, will be affected by the distance between the aspiration opening and the active electrode. The distal tip of the aspiration tube is generally positioned several millimeters proximal to the active electrode so as to not to obstruct the surgeon's view of the electrode during use. Decreasing this distance is desirable since doing so will increase the effectiveness of the aspiration; however, this must be accomplished without limiting the surgeon's view or decreasing the ablator's ability to access certain structures during use. Examples of high-flow aspirating ablators systems include the Three Rib-Aspirating ablators by Linvatec Corporation and the 2.3 mm and 3.5 mm Suction Sheaths for the VAPR system by Mitek Products, the sheaths being used with standard VAPR ablation probes.

Arthrex, Incorporated (Naples, Fla.) markets aspirating ablators in which the aspiration port is in the distal-most surface of the device, and the aspiration path runs through the device. These devices have higher flow rates than low-flow ablators, though less than the high-flow models previously herein described.

Low-flow ablators are characterized by the aspiration of bubbles and fluid through gaps in the ablating surfaces of the active electrode, conveying them from the surgical site via means in the elongated distal portion of the device. Because the low-flow aspiration tends to draw hot saline from the active site of a thermal process, current low-flow ablators require increased power to operate as effectively as a non-aspirating or high-flow aspirating ablators. In the case of low-flow ablators, the heat removed is necessary process heat rather than the waste heat removed by high-flow ablators. Because of this, aspirating ablators of the low-flow type generally require higher power levels to operate than other ablators thereby generating more waste heat and increasing undesirable heating of the fluid within the joint. Typical of low-flow aspirating ablators are those produced by Arthrocare and Smith and Nephew.

Each of these types of aspirating ablator electrodes has its drawbacks. In the case of high-flow aspirating ablators, the aspiration tube increases the diameter of the device, thereby necessitating the use of larger cannulae. In the case of low-flow aspirating ablators, aspiration decreases the efficiency of the probes since process heat is removed from a thermal process. This decreased efficiency results in decreased rates of tissue removal for a given power level. In turn, this results in increased procedure times or necessitates the use of higher power levels to achieve satisfactory tissue removal rates. Both increased procedure time and high power level usage are undesirable as they cause increased heating of the fluid at the site and thereby the likelihood of thermal injury to the patient.

U.S. Pat. No. 6,840,937 to Van Wyk discloses an aspirating ablator that minimizes the removal of process heat by placing aspiration ports at a distance from the active electrode, specifically in the distal end of the probe, and in the top surface of the ablator, the top aspiration port being surrounded by the insulator that surrounds the active electrode and the port being displaced a short distance from the active electrode. Aspiration ports positioned in this manner remove debris and aspiration byproducts from regions adjacent to the active electrode rather than through the active electrode in the manner of low-flow ablators thereby minimizing the loss of process heat. However, the construction taught by Van Wyk is not well suited to ablators other than 90-degree ablators, in which the aspirating surface is substantially parallel to the tube axis. The distal portion of the device may be bent to create other angles to the tube axis; however, the bend would be proximal to the distal end assembly and would have a relatively large radius such that the finished product would have to be used with large cannulae, an undesirable condition.

U.S. Pat. No. 7,837,683 to Carmel, et al. (herein incorporated by reference in its entirety) describes an aspirating ablator that has an aspiration port in the center of the active electrode. The aspiration port is surrounded by a tubular portion (i.e., wall) that both restricts flow between protuberances surrounding the port and causes aspiration of liquids from regions above (distal to) the ablating surface. The efficiency of the Carmel ablator is increased since the amount of process heat removed is reduced; however, the construction of the device is somewhat complex. Producing ablators of various angles using the construction suggested by Carmel requires that the distal end of the ablator be bent in the same manner as that of the Van Wyk embodiment. The resulting ablator is again too large to be used in small cannulae.

Many surgical procedures are not performed inside a natural or formed body cavity and as such are not performed on structures submerged under a conductive liquid. In laparoscopic procedures, for instance, the abdominal cavity is pressurized with carbon dioxide to provide working space for the instruments and to improve the surgeon's visibility of the surgical site. Other procedures, such as oral surgery, the ablation and necrosis of diseased tissue, or the ablation of epidermal tissue, are also typically performed in an environment in which the target tissue is not submerged. In such cases, it is necessary to provide a conductive irrigant to the region surrounding the active electrode(s), and frequently also to aspirate debris and liquid from the site. Such irrigant may be applied by a means external to the instrument; however, having an irrigation means internal or attached to the instrument generally provides better control and placement. This is also true for aspiration of fluid and debris. External means may be used for aspiration from the site; however, aspiration through the instrument distal end provides improved fluid control and may, in some cases, draw tissue toward the active electrode thereby enhancing performance. U.S. Pat. No. 7,566,333 to Van Wyk, et al. (herein incorporated by reference in its entirety) discloses an electrosurgical device for use in a dry or semi-dry environment.

Electrosurgical devices having means for irrigating a site, and/or means for aspirating fluid, bubbles and debris from a site are well known. Smith, in U.S. Pat. No. 5,195,959, disclose an electrosurgical device with suction and irrigation. Bales, et al., in U.S. Pat. No. 4,682,596 discloses a catheter for electrosurgical removal of plaque buildup in blood vessels, the catheter having lumens for supplying irrigant to the region of the instrument distal tip and for aspirating debris from the region. Hagen, in U.S. Pat. No. 5,277,696 discloses a high frequency coagulation instrument with means for irrigation and aspiration from the region of the instrument tip. Pao, in U.S. Pat. No. 6,674,499, discloses a coaxial bipolar probe with suction and/or irrigation. Eggers, in U.S. Pat. No. 6,066,134, discloses a method for electrosurgical cutting and coagulation that uses a bipolar probe having means for irrigating and aspirating from the region of the probe distal tip. The Eggers device uses the irrigant flow to provide a return path to a return electrode recessed axially a distance away from the active electrode(s).

As in the case with ablators operating in a fluid filled cavity, for those operating in a dry or semi-dry environment with supplied irrigant, the placement and volume of aspiration flow through an electrosurgical instrument in the region of an active electrode, or even through the active electrode, may adversely affect the performance of the instrument. Electrosurgery, particularly procedures in which tissue is vaporized, is a thermal process. Aspiration which draws fluid through or around the active electrode surfaces draws away process heat, thereby decreasing heating of the conductive irrigant in the region so as to decrease bubble production and ablative arcing. This makes the device less efficient thereby requiring increased power to achieve acceptable performance.

The construction of aspirating ablator distal portions (those distal to the handle) may be divided into two types: complex construction in which power is conducted to the active electrode by wires housed within a tubular distal portion, and simple construction in which the elongated tubular structure conducts power to the active electrode.

Aspirating ablation devices with complex construction have a return electrode attached to the probe, the tubular portion conducting RF energy from the return electrode to the handle assembly, from which it is returned to the generator. This tubular return portion must be electrically isolated from the active electrode and wiring within the tubular portion that conducts power to the active electrode. Additionally, the tubular portion must house a dielectric tube for conducting the aspirated materials from the device distal tip to the handle, and therethrough to an external vacuum supply. Aspiration flow must be isolated from the tubular return structure since the conductive liquid contained in the flow is in contact with the active electrode and therefore at high potential. Ablation devices having complex construction are those from Arthrocare, Smith and Nephew, Mitek division of Johnson and Johnson, and Stryker.

Aspirating ablation devices with simple construction use a return electrode in the form of a dispersive pad that is removably applied to the patient's body remote to the surgical site. The distal portion of these device is a metallic tube, to the distal end of which is mounted an active electrode, the RF energy being conducted to the electrode by the tube. Aspirated materials are conducted from the distal tip of the device to the handle, and therethrough to an external vacuum supply. Because the flow is at the same high potential as the tube, it is not necessary to electrically isolate it from the tube. Typical of aspirating ablators having a simple construction are the Lightwave Suction Ablator by Linvatec, and the 9800 series aspirating ablators by Arthrex.

Ablators having an ablating surface with a normal perpendicular to that of the device axis ("90 degree ablators") are the most popular configuration with surgeons, however, ablators are produced in a variety of configurations with the normal to the ablating surface inclined to the axis at angles ranging between thirty and ninety degrees. Ablators having a complex construction are formed to each unique angle using components specific to that geometry. For instance, the distal-end components used to create a 90-degree ablator are configured differently from those used to create a 60-degree ablator, which are different from those used to create a 30-degree ablator. Mitek produces a "VAPR-T Side-Effect ablator" and a "VAPR-T Reverse-angled Side-Effect ablator" from the same components, the tubular element being bent proximal to the distal electrode assembly, however, because of the bend in the tube the ablator cannot be inserted into a standard small-diameter cannula frequently used for fluid control in shoulder and knee surgery.

In the case of ablators having simple construction, non-aspirating ablators of various angles of a particular configuration (for example 3.4 mm 30-, 60- and 90-degree) may be constructed using common components. For instance, 30, 60 and 90 degree Ultrablators by Linvatec use a common active electrode component and insulator, the active electrode component being bent to the required angle to create the various products. Similarly, Arthrex 45 and 90 degree small joint and meniscectomy ablators have common active electrode components, the distal ablating surface of the component being beveled at 45 degrees to form the 45-degree ablator. The distal end of the element is bent 45 degrees to create a 90-degree ablator.

Prior art aspirating ablators of simple construction (that is, wherein the RF energy is conducted to the active electrode by the elongated tubular distal element) have an active electrode and distal aspiration path formed by an assembly of at least two elements, generally an active electrode element and an element to provide an aspiration path from the aspiration port to the tubular element. This two-piece construction has two associated disadvantages: first, depending on the specific design, the complexity may increase manufacturing difficulty and cost; and second, the complexity may make it difficult to use common components to produce ablators having a range of angular displacement between ablating surface and tube device axis while maintaining a profile that allows use of the device in small diameter cannulas. For instance, Van Wyk in U.S. Pat. No. 6,840,937, Carmel, et al. in co-pending application Ser. No. 11/431,515, teach aspirating ablators with distal electrode assemblies formed from an electrode element and a tubular element for providing an aspiration path, both elements being of a simple, easy to manufacture design that can be produced at low cost. However, if the assembly is bent in such a way that ablators having a range of angles between the surfaces can be formed with the same components, the resulting profile of the bent devices will be such that they cannot pass through small diameter cannulas. Gallo, et al. in co-pending application Ser. Nos. 11/636,548 and 12/639,644 teaches assemblies of complex, difficult to machine components joined by laser welding. While these ablator assemblies can be bent to some degree to produce ablators having a range of angles between the ablating surfaces and the device axis and with the resulting ablators being able to pass through fairly small cannulas, the cost of manufacturing these assemblies is high.

There is a need for an aspirating ablator having a simple construction in which the aspiration flow removes primarily waste heat rather than process heat; and which is constructed so that a single component or set of components can be used to produce at low cost ablators of various angles which may be used with small cannulae for arthroscopy, or in a semi-dry environment.

SUMMARY OF THE INVENTION

It is accordingly an objective of the present invention to provide a highly efficient aspirating electrosurgical ablator capable of overcoming the deficiencies discussed above. More particularly, in view of the ever-present need in the art for improvements in electrode design, it is an objective of the present invention to provide an effective, efficient aspirating ablator that has a simple form, may be produced at low cost and is suited to the bulk vaporization of a wide variety of tissue, in a wide array of environments. To that end, an additional objective of this invention to provide active electrode fabricated as a single machined component that can be flexed into a number of bent positions, to give rise to a range of ablating surface angles (i.e., the angle between the ablating surface and the axis of the ablation device).

Thus, in view of the above, the present invention provides an aspirating electrosurgical ablator for bulk vaporization of tissue characterized by a distal end active element of a unitary construction, preferably fabricated from a monolithic piece of homogeneous metallic material. The ablator preferably includes a proximal portion forming a handle, a distal portion that includes the active element and a central lumen extending from the proximal portion to the distal portion, stopping short of the distal end. In a particularly preferred embodiment, the active element is a closed-end tubular element having protuberances, grooves or other contours machined into its distal end to create regions of high current density and yield an angled or beveled ablating surface. The angle of the ablating surface is characterized by the angle a line normal to the ablating surface forms with the longitudinal axis of the distal portion of the tubular element. In a preferred embodiment, this angle ranges between 30 and 80 degrees, and more preferably between 40 and 70 degrees.

The active element is further characterized by cannulated lumen, preferably centralized and suited for aspiration extending therethrough and terminating in a lateral opening (aspiration port) positioned just proximal and therefore adjacent to said ablating surface. This novel configuration of lateral aspiration port and beveled, contoured ablation surface permits ablation and vaporization to occur simultaneously, without significantly impacting process heat dispersal and/or negatively affecting ablation efficiency.

Accordingly, in a preferred embodiment, the present invention provides an active electrode for connection to an electrosurgical device for the bulk vaporization of tissue, the active electrode including a cannulated tubular element formed from a single piece of homogenous metallic material and characterized by an open proximal end, a closed distal end and a preferably centralized lumen extending therebetween, the active electrode further characterized by:

a) a tubular distal portion having a beveled distal-most ablation surface that forms an acute angle with the longitudinal axis of said distal portion, b) a raised flange portion proximally adjacent to the tubular distal portion having a diameter greater than the diameter of the tubular distal portion and a flat distal-facing surface, c) a tubular middle portion proximally adjacent to said flange portion, wherein the tubular middle portion and the tubular distal portion are not coaxial, further wherein the longitudinal axis of the tubular middle portion forms a predetermined acute angle with the longitudinal axis of said tubular distal portion, d) a tubular proximal portion configured for attachment to an elongate cannulated tubular member, and e) a lateral opening formed in a side wall of the tubular distal portion and positioned proximally to said beveled ablation surface, said opening extending through the side wall of said distal portion into the central lumen.

The active electrode of the present invention may be fabricated by any suitable method, including, for example, by metal injection molding as either a single unitary element, or as two sub-elements that are subsequently fused into a single unitary element during sintering. For example, an active metal electrode as described above, including a (a) tubular distal portion of a predetermined length having an angled distal most surface, (b) a flange portion proximally adjacent to the tubular distal portion having a diameter greater than the diameter of said tubular distal portion and having a distal-facing surface, and (c) a tubular proximal-most portion is formed for attachment to an elongated cannulated member, as well as a central lumen extending from the proximal end of said the active electrode to a predetermined depth and terminating in a lateral opening disposed on the exterior surface of said tubular distal portion, may be fabricated by (i) first molding the active metal electrode as a single linear unit and then (ii) bending the tubular middle portion to a pre-determined acute angle such that tubular distal portion and said tubular middle portion are not coaxial. Alternatively, the active metal electrode may be pre-formed in the bent configuration or assembled into a bent configuration from separately molded components.

The proximal end of the active electrode piece may be readily affixed to the distal end of the elongate tubular cannula element that constitutes the distal portion of an electrosurgical ablation device. The proximal portion of the ablation device includes a handle that may be, in turn, connected to a suitable vacuum source such that the aperture adjacent and just proximal to the beveled ablating surface, the central lumen of the active electrode piece, and the lumen of the cannula portion together form an aspiration path such that byproducts of ablation may be removed from the region surrounding the distal end of the device during use.

The unitary active element piece described above preferably further includes a tubular insulator having open proximal and distal ends and formed from a suitable dielectric material, the insulator configured to slide over and surround the distal end of the electrode. In use, the proximal end of the insulator abuts a raised or flanged, preferably radiused, portion of active element acting as a stop therefore. The distal end of the tubular insulator includes an angled planar surface analogous to and coordinating with the beveled ablation surface disposed on the distal end of the active element. When the insulator is assembled to the active electrode piece, the beveled ablating surface protrudes through the distal portion of the distal opening of the insulator a predetermined distance, and the open proximal end allows communication between the region distal to the insulator and the lateral aperture (i.e., aspiration port) disposed in the electrode piece. The beveled ablating surface is then parallel to the angled distal surface of the insulator.

Except for the portion of the electrode piece protruding beyond the insulator distal surface, the electrode piece and elongate tubular member are preferably insulated by a dielectric coating that overlaps the proximal end of the insulator. Additionally, with the exception of the distal insulator component and the proximal cannula component, the remainder of the active electrode component constitutes a unitary, integral construction, preferably fabricated from a homogenous single piece of metallic material.

Accordingly, in another preferred embodiment, the present invention provides an electrosurgical device for the bulk vaporization of tissue including an active electrode such as described above, including an elongate cannulated tubular element affixed to the proximal portion of the active electrode and further including a tubular insulator formed from a suitable dielectric material. In a particularly preferred embodiment, the insulator has an open proximal end characterized by a first proximal-most surface and an open distal end characterized by a second distal-most surface, such that when the insulator is positioned about the tubular distal portion of the active electrode, the first proximal-most surface of the insulator abuts the distal-facing surface of the flange portion and the second distal-most surface of the insulator is slightly proximal to the beveled ablation surface of the active electrode such that the lateral opening, the active electrode central lumen, and the cannulated tubular element provide a continuous aspiration path allowing the flow of vaporization byproducts from the region adjacent to the beveled ablation surface and to the proximal end of the electrode tubular element. The electrosurgical device may optionally further include a dielectric coating covering the exterior of the tubular element, the portion of the active electrode proximal to said insulator, and a proximal portion of said insulator.

The active element preferably includes a portion of reduced wall thickness disposed proximate to the proximal end of the insulator when assembled to the electrode piece, the reduced wall thickness affording flexibility to the active element, permitting it to be bent, the bend occurring primarily in the region of reduced wall thickness. Flexing and bending of the active electrode piece allows the distal end ablating surface to be oriented at a wide range of angles and therefore find utility in connection with a wide variety of electrosurgical products. For instance, bending the element to an angle that is the complement of the angle formed between a line normal to the ablating surface and the axis of the element distal portion in the direction of the aperture (hereinafter referred to as "upward") the normal to the ablating surface can be made perpendicular to the axis of the tubular element to form what is commonly referred to as a "90 degree ablator". As an example, if the first ablation surface angle (characterized by a line normal to the ablating surface and the longitudinal tube axis) is 60 degrees, in its unbent state the finished product would be referred to in the industry as a "60 degree ablator". Converting the active electrode piece to the upward configuration, such that the second angle is 30 degrees would result in the creation of a "90 degree ablator". Bending the electrode piece downward (away from the aperture) 15 degrees would make the angle between the normal to the ablating face and the tube axis 45 degrees so as to create a "45 degree ablator". In this fashion, a single unitary piece active element configured for connection to any number of conventional electrosurgical device can be used to produce a variety of ablator products appropriate for a range of tissues and procedures.

Because the active electrode piece is bent only moderately to form the various products (generally less than the complement of the first angle), and because the bend is localized at a distal location just proximate to the proximal end of the insulator, the ablators whether unbent or bent, fit into cannulae having relatively small inner diameters. In this manner, insertion trauma may be reduced.

Due to its location proximal to the ablating surface, the aspiration port primarily removes waste heat rather than process heat. The aspiration port may be made quite large relative to the size of the ablating surface so as to allow efficient removal of ablation byproducts without clogging. If clogging occurs, the size of the aspirating port and its readily accessible, unobstructed location allow easy clearing of the clogging tissue either by wiping on a suitable surface or by the insertion of a wire into the aspiration port.

The aspiration port allows substantial aspiration flow through the electrode piece thereby removing waste heat from the ablation process. Cooling of the electrode piece in this manner prevents failure of the dielectric coating which covers the assembly and also guards against overly high local temperatures which can, in turn, give rise to tissue injury.

A final objective of the present invention is to provide a method for forming an active electrode of the present invention, the method including the steps of: [0046] (a) on a screw-machine, lathe or other suitable turning machine, forming a metal blank having a tubular distal portion of a predetermined length, a flange portion having a diameter greater than the diameter of said tubular distal portion and having a distal-facing surface, said flange portion being proximally adjacent to said tubular distal portion, a tubular middle portion proximal to said flange portion, a tubular proximal-most portion formed for attachment to an elongated cannulated member, and a central lumen extending from the proximal end of said active electrode to a predetermined depth; [0047] (b) beveling the distal end of said blank to form an angled distal most surface on said blank; [0048] (c) forming a lateral opening between the exterior surface of said tubular distal portion and the central lumen; and [0049] (d) bending the tubular middle portion a pre-determined acute angle such that tubular distal portion and said tubular middle portion are not coaxial.

These and other objects are accomplished in the invention herein disclosed which is an aspirating electrosurgical ablator of simple construction. It will be understood by those skilled in the art that one or more aspects of this invention can meet certain of the above objectives, while one or more other aspects can meet certain other objectives. Each objective may not apply equally, in all its respects, to every aspect of this invention. As such, the preceding objects should be viewed in the alternative with respect to any one aspect of this invention.

The above-noted objects and features of the invention will become more fully apparent when the following detailed description is read in conjunction with the accompanying figures and/or examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of electrode design. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE FIGURES

Various aspects and applications of the present invention will become apparent to the skilled artisan upon consideration of the brief description of the figures and the detailed description of the present invention and its preferred embodiments which follows:

FIG. 2 depicts an electrosurgical device constructed in accordance with the principles of this invention FIG. 3 is a perspective view of the objects of FIG. 2.

FIG. 11 is a plan view of an electrode piece for an electrosurgical ablator formed in accordance with the principles of this invention.

FIG. 12 is a side elevational view of the objects of FIG. 8.

FIG. 13 is a sectional view of the objects of FIG. 8 at location A-A of FIG. 8.

FIG. 19 is a plan view of the distal end assembly of an ablator formed in accordance with the principles of this invention.

FIG. 20 is a side elevational view of the objects of FIG. 16.

FIG. 21 is a sectional view of the objects of FIG. 16 at location A-A of FIG. 16.

FIG. 31 is a plan view of an active electrode for an alternate embodiment of this invention.

FIG. 32 is a side elevational view of the objects of FIG. 31.

FIG. 33 is a side elevational sectional view of the objects of FIG. 31 at location A-A of FIG. 31.

FIG. 34 is a distal axial view of the objects of FIG. 31.

FIG. 35 is a perspective view of the objects of FIG. 31.

FIG. 54 is a perspective view of the formed active element of embodiment of FIG. 50 mounted to a tubular member.

FIG. 55 is a plan view of the objects of FIG. 51.

FIG. 56 is a side elevational view of the objects of FIG. 51.

FIG. 57 is a side elevational sectional view of the objects of FIG. 54 at location A-A of FIG. 55.

DETAILED DESCRIPTION OF THE PREFERRED EMBODIMENTS

Figure 1:
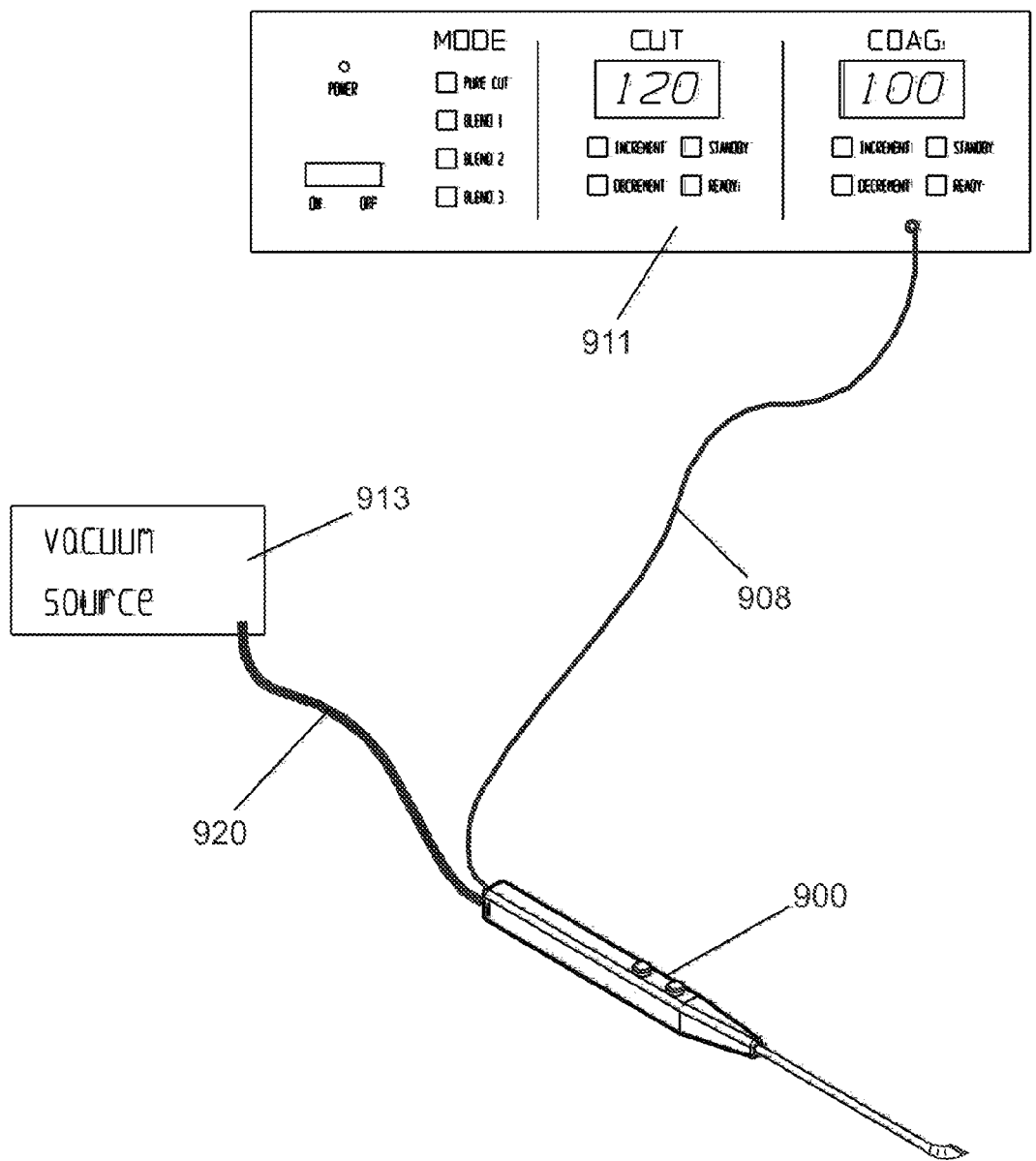
FIG. 1 is a schematic representation of an electrosurgical system for bulk vaporization of tissue constructed in accordance with the principles of this invention.
Figure 4:
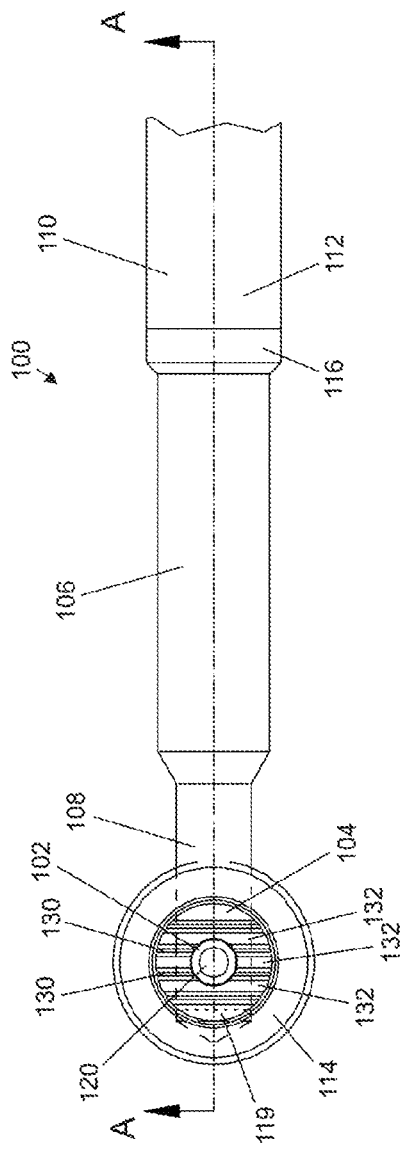
FIG. 4 is a plan view of the distal portion of a prior art electrosurgical ablator.
Figure 6:
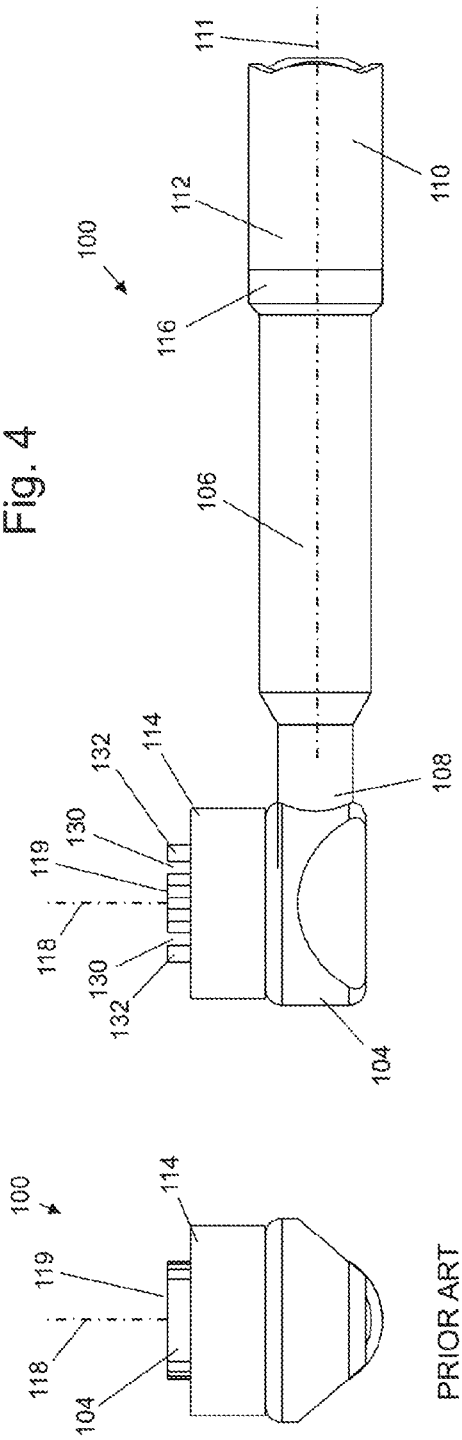
FIG. 6 is an axial elevational view of the objects of FIG. 1.
Figure 5:
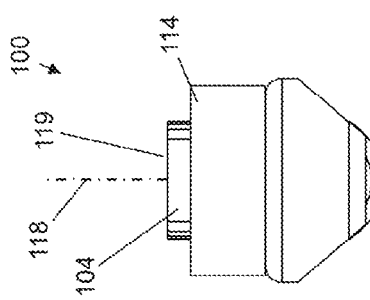
FIG. 5 is a side elevational view of the objects of FIG. 1.
Figure 7:
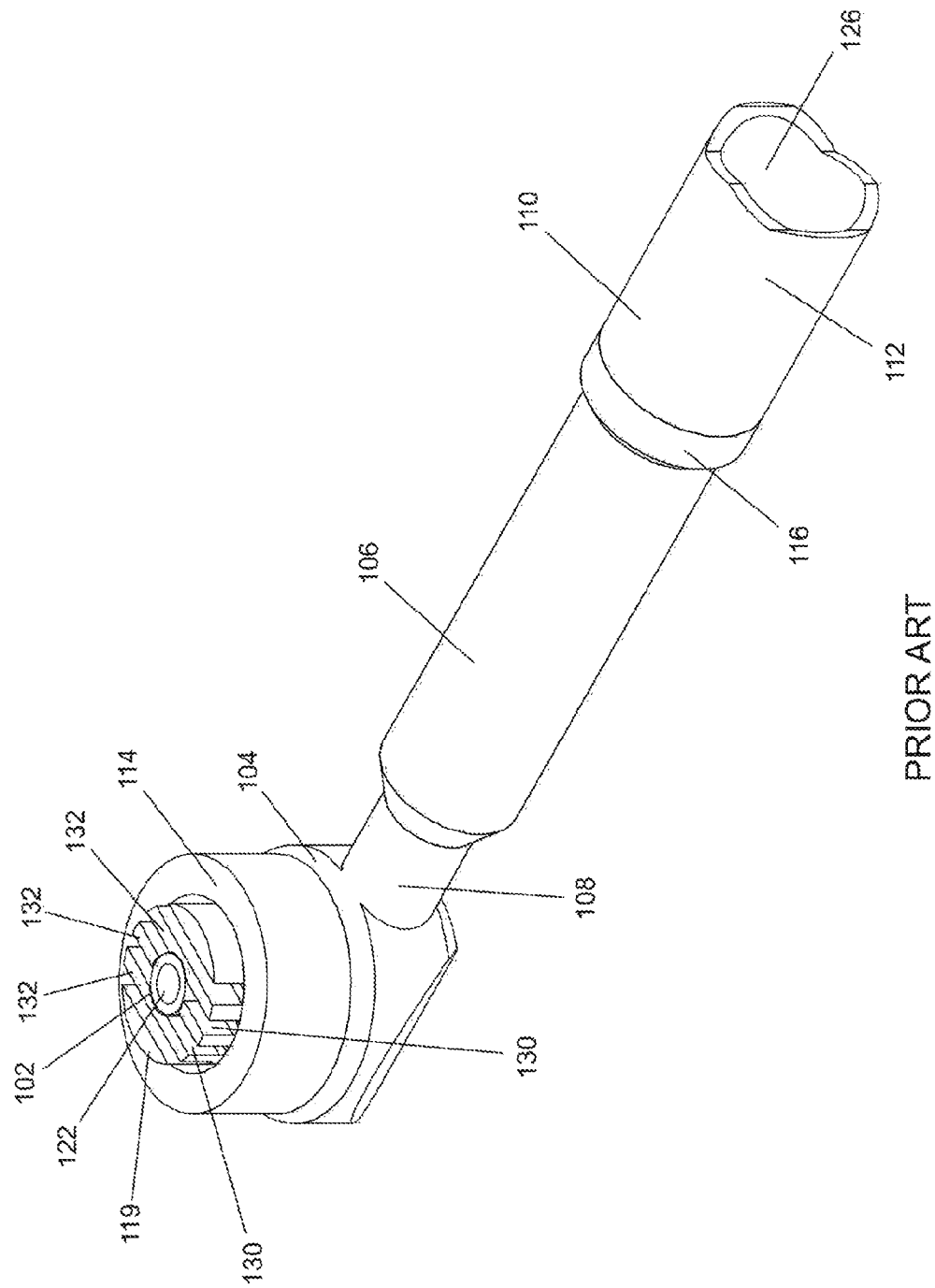
FIG. 7 is a perspective view of the objects of FIG. 1.
Figure 8:
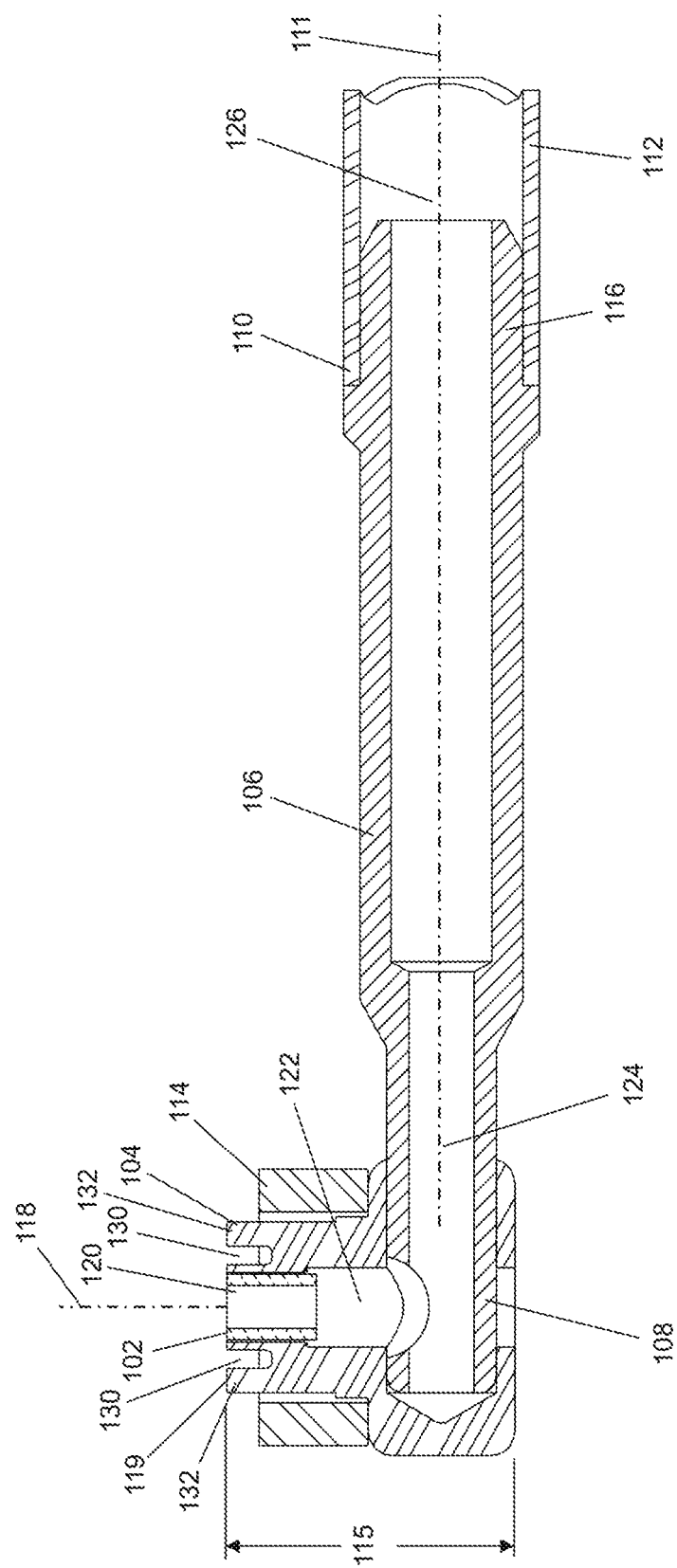
FIG. 8 is a sectional view of the objects of FIG. 1 at location A-A of FIG. 1.

The present invention constitutes a marked improvement in the field of electrosurgery, more particularly, to high efficiency surgical devices and methods which use radio frequency (RF) electrical power to vaporize and remove all or part of a tissue mass.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Elements of the Present Invention

In the context of the present invention, the following definitions apply:

The words "a", "an", and "the" as used herein mean "at least one" unless otherwise specifically indicated.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as electrosurgical "probes" or "instruments".

The present invention is particularly concerned with the category of electrosurgical instruments referred to in the art as "ablators", i.e., electrosurgical electrodes designed for the bulk removal of tissue by vaporization rather than the cutting of tissue or coagulation of bleeding vessels.

The present invention makes reference to an "active electrode" or "active element". As used herein, the term "active electrode" refers to one or more conductive elements formed from any suitable metallic material, such as stainless steel, nickel, titanium, tungsten, and the like, connected, for example via cabling disposed within the elongated proximal portion of the instrument, to a power supply, for example, an externally disposed electrosurgical generator, and capable of generating an electric field.

The present invention makes reference to a "return electrode". As used herein, the term "return electrode" refers to one or more powered conductive elements to which current flows after passing from the active electrode(s) back to the electrical RF generator. This return electrode may be located on the ablator device or in close proximity thereto and may be formed from any suitable electrically conductive material, for example a metallic material such as stainless steel, nickel, titanium, tungsten, aluminum and the like. Alternatively, one or more return electrodes, referred to in the art as "dispersive pads" or "return pads", may be positioned at a remote site on the patient's body.

The present invention makes reference to "fluid(s)". As used herein, the term "fluid(s)" refers to liquid(s), either electrically conductive or non-conductive, and to gaseous material, or a combination of liquid(s) and gas(es).

The term "proximal" refers to that end or portion which is situated closest to the user; in other words, the proximal end of an electrosurgical instrument of the instant invention will typically include the handle portion.

The term "distal" refers to that end or portion situated farthest away from the user; in other words, the distal end of an electrosurgical instrument of the instant invention will typically include the active electrode portion.

The present invention makes reference to the vaporization of tissue. As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. The present invention is not limited in terms of the tissue to be treated but rather has broad application to the vaporization any target tissue with particular applicability to the ablation, destruction and removal of problematic joint tissues.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Unless otherwise defined, all technical and scientific terms used herein have the same meaning as commonly understood by one of ordinary skill in the art to which this invention belongs. In case of conflict, the present specification, including definitions, will control.

Utilities of the Present Invention

As noted above, the present invention is directed to high efficiency electrosurgical instruments and methods which utilize radio frequency (RF) energy to vaporize soft tissues, having particular utility in the context of arthroscopy and the removal of problematic joint tissues. However, the invention is not restricted thereto. Aspects are equally applicable to other uses, for example in connection with oncological, ENT, urological, gynecological, and laparascopic procedures, as well as in the context of general surgery.

Similarly, while some embodiments utilize the endogenous fluid of a "wet field" environment to transmit current to target sites, others require an exogenous irrigant. In certain embodiments, the "irrigant" (whether native or externally applied) is heated to the boiling point, whereby thermal tissue treatment arises through direct contact with either the boiling liquid itself or steam associated therewith. This thermal treatment may include desiccation to stop bleeding (hemostasis), and/or shrinking, denaturing, or enclosing of tissues for the purpose of volumetric reduction (as in the soft palate to reduce snoring) or to prevent aberrant growth of tissue, for instance, endometrial tissue or malignant tumors.

Liquids (either electrically conductive or non conductive) and gaseous irrigants, either singly or in combination may also be advantageously applied to devices for incremental vaporization of tissue. Normal saline solution may be used. Alternatively, the use of low-conductivity irrigants such as water or gaseous irrigants or a combination of the two allows increased control of the ablating environment.

The electrosurgical devices of the present invention may be used in conjunction with existing diagnostic and imaging technologies, for example imaging systems including, but not limited to, MRI, CT, PET, x-ray, fluoroscopic, thermographic, photo-acoustic, ultrasonic and gamma camera and ultrasound systems. Such imaging technology may be used to monitor the introduction and operation of the instruments of the present invention. For example, existing imaging systems may be used to determine location of target tissue, to confirm accuracy of instrument positioning, to assess the degree of tissue vaporization (e.g., sufficiency of tissue removal), to determine if subsequent procedures are required (e.g., thermal treatment such as coagulation and/or cauterization of tissue adjacent to the target tissue and/or surgical site), and to assist in the traumatic removal of the device.

As noted above, the electrosurgical instruments of the present invention find utility in bulk tissue vaporization. The flexible design permits the distal active end to exhibit a wide array of angled profiles. Certain configurations will have particular utility in the treatment of protruding or projecting tissues while others will be optimized for tissue surface treatment. Accordingly, the present invention is not particularly limited to the treatment of any one specific disease, body part or organ or the removal of any one specific type of tissue, the components and instruments of the present invention.

Illustrative Embodiments of the Present Invention

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Referring to the figures, FIG. 1 depicts an electrosurgical system constructed in accordance with the principles of this invention. Ablator electrode 900 is connected by electrical cable 908 to electrosurgical generator 911, and by tube 920 to an external vacuum source. A return electrode (not shown) is connected to the electrosurgical generator to provide a return path for the RF energy. The return electrode may be a dispersive pad attached to the patient at a site remote from the surgical site, or may be in proximity to the active electrode in contact with tissue or the conductive liquid.

FIGS. 2 and 3 further depict the details of electrosurgical instrument 900 constructed in accordance with the principles of this invention. Instrument 900, also referred to herein as an "ablator", has a proximal portion 902 forming a handle and an elongated distal portion 904. Handle 902 has passing from its proximal end 906 electrical cable 908 which is connected to electrosurgical generator 911, and flexible tube 910 which is connected to tube 920 and thereby to external vacuum source 913. Near distal end 912 of handle 902, first activation button 914 labeled "ablate" and second activation button 916 labeled "coagulate", protrude from top surface 918 of handle 902. Elongated distal portion 904 has a proximal end 920 that is mounted to distal end 912 of handle 902, and a distal end 922.

To best understand the principles of this invention, it is necessary to consider a prior art aspirating ablator. The distal portion 100 of a prior art aspirating device is depicted in FIGS. 4 through 8. Tube 102 is affixed to active electrode 104 which is affixed to distal end 108 of tubular elongate element 106, the proximal end 116 of which is assembled to the distal end 110 of tube 112. Insulator 114 surrounds the upper portion of active electrode 104. Lumen 120 of tube 102, lumen 122 of active electrode 104, lumen 124 of tubular elongate element 106, and lumen 126 of tube 112 together form an aspiration path for removal of heated fluid, bubbles and debris products of ablation during use, lumen 126 of tube 112 being in communication with a vacuum source. Tube 102 prevents flow of liquid through grooves 130 between ribs 132 thereby minimizing removal of process heat so as to increase the efficiency of the prior art ablator. Distal portion 100 is covered with a suitable dielectric material except for the upper portions of active electrode 104 and insulator 114. Dotted line 118 is normal to the ablating surface.

Figure 9:
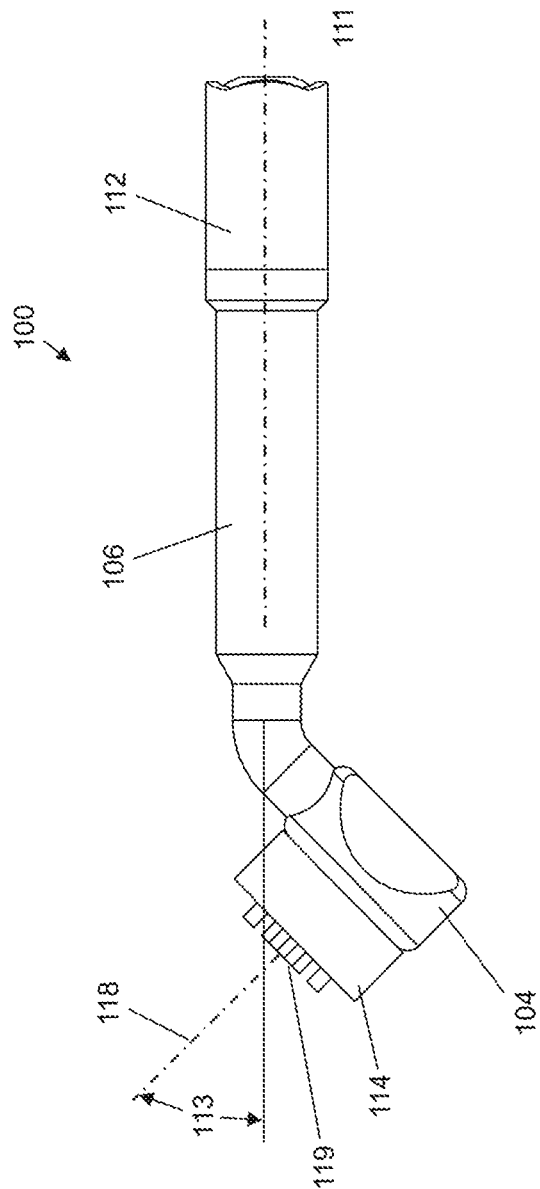
FIG. 9 is a side elevational view of the prior art device objects of FIG. 1 with the tubular element bent downward.
Figure 10:
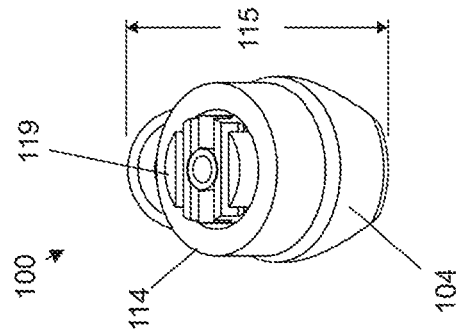
FIG. 10 is an axial elevational view of the objects of FIG. 6.
Figure 15:
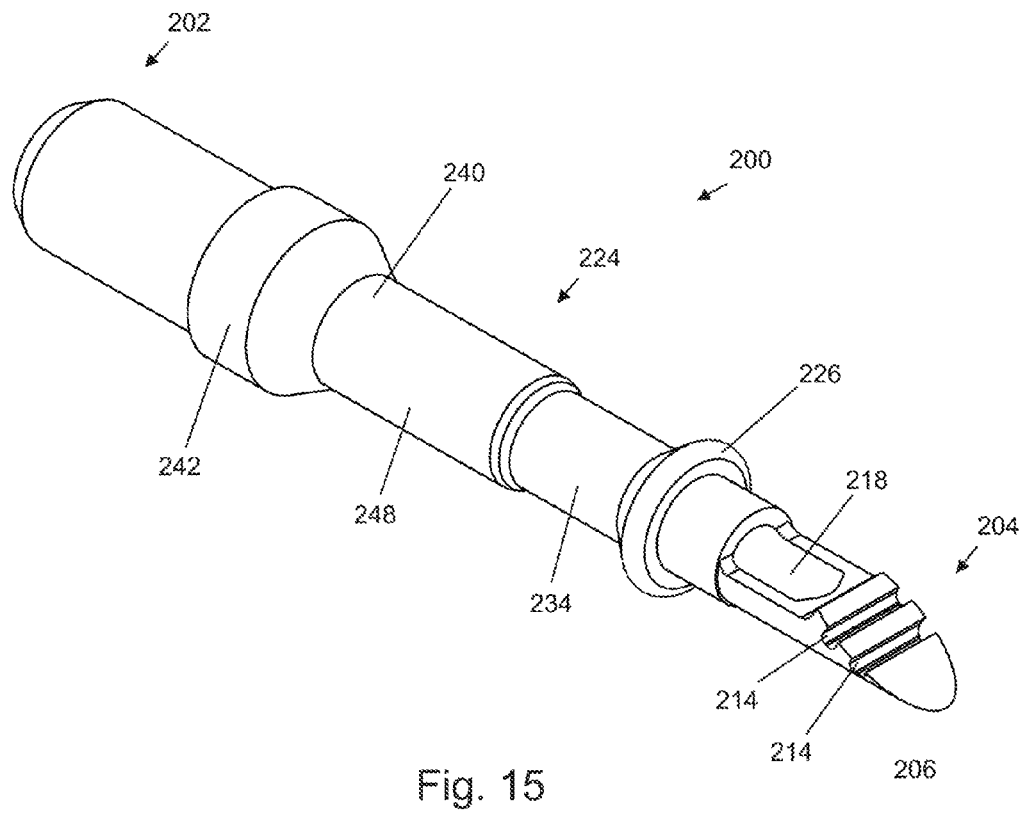
FIG. 15 is a perspective view of the elements of FIG. 8.
Figure 14:
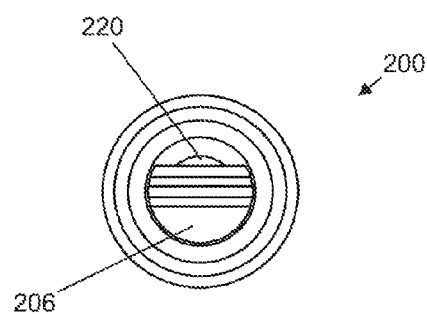
FIG. 14 is an axial elevational view of the objects of FIG. 8.

As shown in FIGS. 4 through 8, distal end 100 forms a "90 degree" ablator, a normal 118 to the upper, ablating surface 119 of active electrode 104 being normal to the axis of tubular member 106 and tube 110. FIGS. 9 and 10 depict a distal portion 108 of tubular elongate element wherein the distal end is bent, formed downward so that line 118 normal to ablating surface 119 forms an angle 113 with axis 111 of member 106. Bending in this manner increases the overall height of distal portion 100 to height 115.

A distal-end element (active electrode) for an electrosurgical ablator formed in accordance with the principles of this invention is depicted in FIGS. 11 through 15. Active element 200 is formed from a single monolithic metallic material. Active element 200 combines the functions of elongate element 106 and active electrode 104 of prior art assembly 100, such that proximal end 202 of element 200 is configured for mounting to directly the distal end of a tube. Distal portion 204 has an ablating surface 206 formed thereon, wherein a line 208 normal to ablating surface 206 forms an angle 210 with axis 212 of element 200. Ablating surface 206 has integral grooves 214 formed therein. A lateral port or opening 206 that intersects lumen 220 of active element 200 is positioned just proximal to ablating surface 206. Proximal to opening 218, portion 219 of element 200 has an external diameter of 221. Middle portion 224 of element 200 has at its distal end flange 226 having a distal surface 228 perpendicular to the device axis 212, a conical proximal surface 230, and a radiused edge 232 disposed between the distal and proximal surfaces. Sharpened edges increase the electric field on an RF device. Edge 232 is radiused to minimize intensification of the electric field so as to prevent breakdown of the dielectric coating that will cover the completed assembly. Proximal to flange 226, middle portion 224 includes cylindrical portion 234 of diameter 236 that extends distance 238. The proximal end 240 of middle portion 224 has formed thereon a flange 242 having a proximal planar surface 244 to which device axis 212 is normal, and a conical distal surface 246. Distal to distal surface 246, cylindrical portion 248 of diameter 250 extends distally to cylindrical portion 234. Diameter 250 of cylindrical portion 248 is larger than diameter 236 of portion 234 such that bending of element 200 occurs primarily in portion 234. Portion 234 is fabricated to have a reduced resistance to bending as compared to portion 248; for example, portion 234 may be manufactured to have one or more regions of reduced wall thickness. In other embodiments, cylindrical portion 234 of middle portion 224 is eliminated such that middle portion 224 has a constant diameter throughout its entire length. In such embodiments, the length of middle portion 224 is minimized so that bending of portion 224 results in a tight bend radius. Element 200 may be manufactured at low cost using standard machine tools. For instance, a type of lathe commonly referred to as a Swiss-style screw machine may be used to form a cylindrical blank after which a wire electrical discharge machine (wire EDM) may be used to form ablating surface 206, grooves 214 and lateral opening 218.

Figure 16:
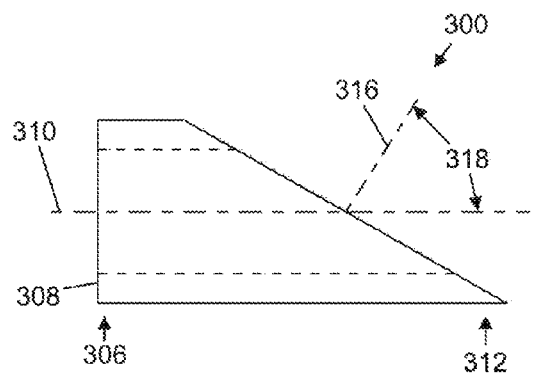
FIG. 16 is a side elevational view of an insulator for an electrosurgical ablator formed in accordance with the principles of this invention.
Figure 17:
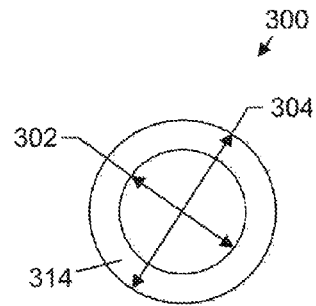
FIG. 17 is an axial elevational view of the objects of FIG. 13.
Figure 18:
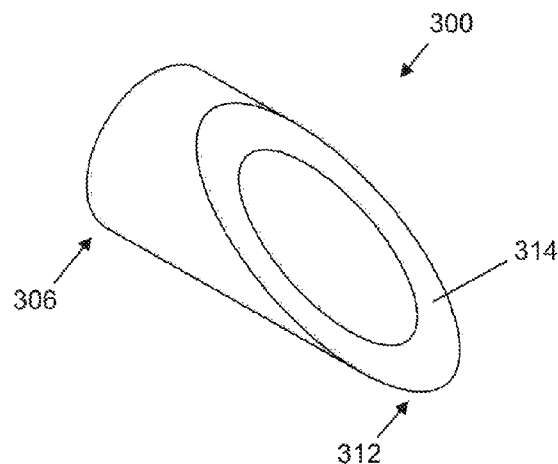
FIG. 18 is a perspective view of the objects of FIG. 13.
Figure 23:
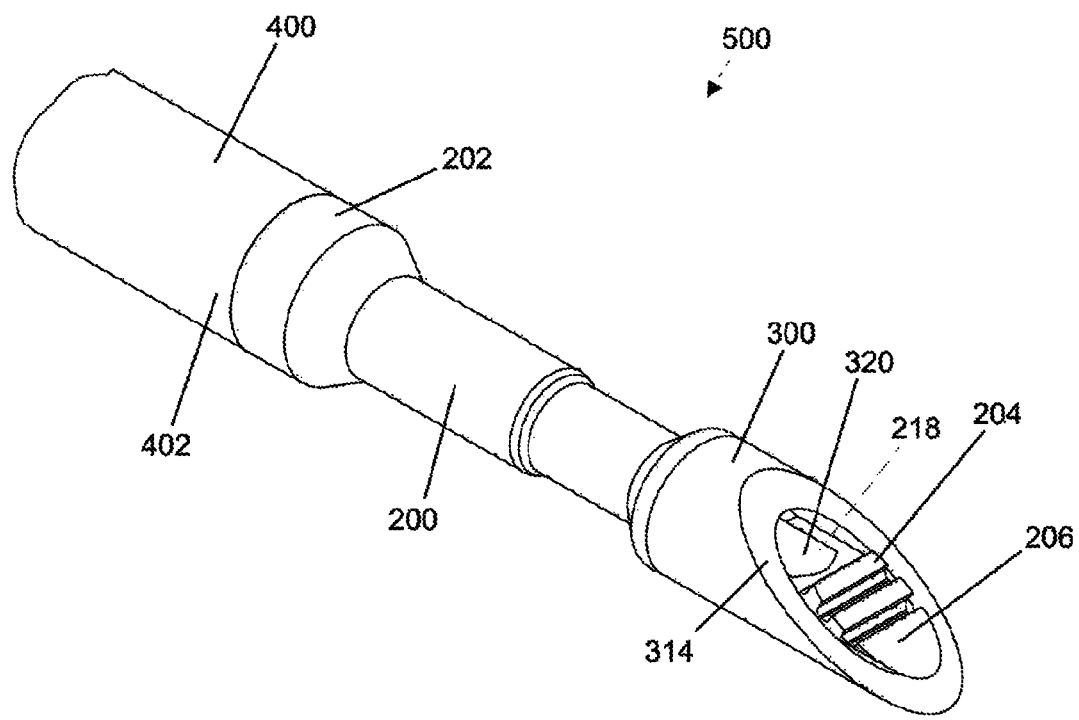
FIG. 23 is a perspective view of the objects of FIG. 16.
Figure 22:
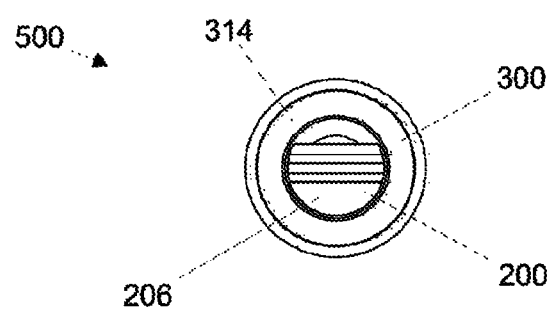
FIG. 22 is an axial elevational view of the objects of FIG. 16.

FIGS. 16 through 18 depict an insulator for an electrosurgical ablator formed in accordance with the principles of this invention. Insulator 300, formed from a suitable dielectric material such as, for instance, alumina, is tubular in form having a lumen 301 with a diameter 302 slightly larger than diameter 221 of portion 219 of element 200, and an outside diameter 304. Insulator 300 has a proximal end 306 with a planar proximal face having a normal parallel to axis 310 of insulator 300. Insulator 300 has a distal end 312 forming a planar surface 314 having a normal 316 angularly displaced from axis 310 at angle 318, angle 318 being approximately equal to angle 210 of element 200. Lumen 301 intersects surface 314 to form distal opening 320.

Referring to FIGS. 19 through 23 depicting the distal end assembly 500 of an electrosurgical ablator constructed in accordance with the principles of this invention. Proximal end 202 of active element 200 is mounted to the distal end 402 of tube 400. Insulator 300 is mounted to distal end 204 of element 200, proximal face 308 of insulator 300 being adjacent to distal face 228 of flange 226 that acts as a stop for insulator 300. Lumen 301 of insulator 300 is centered by portion 219 of active element 200 such that the outer cylindrical surface of portion 204 of active element 200 does not contact the inner surface of lumen 301. Distal face 314 of insulator 300 is parallel to ablating surface 206 and is displaced from ablating surface 206 distance 502. Tubular member 400 is assembled to proximal end 240 of middle portion 224 of active element 200, with distal end 402 of member 400 abutting proximal surface 244 of flange 242 of active element 200. Distal opening 320 and lumen 301, lumen 220 of element 200, and lumen 404 of tubular member 400 provide an aspiration path between the region distal to distal surface 314 and a vacuum source connected via means within the handle to lumen 404 of tubular member 400. A dielectric coating covers assembly 500 proximal to line 510.

Figure 25:
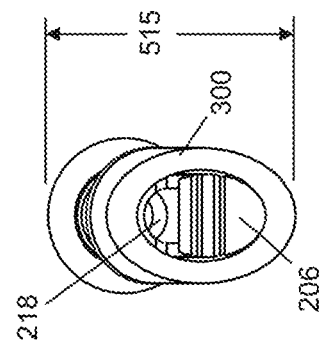
FIG. 25 is an axial elevational view of the objects of FIG. 21.
Figure 24:
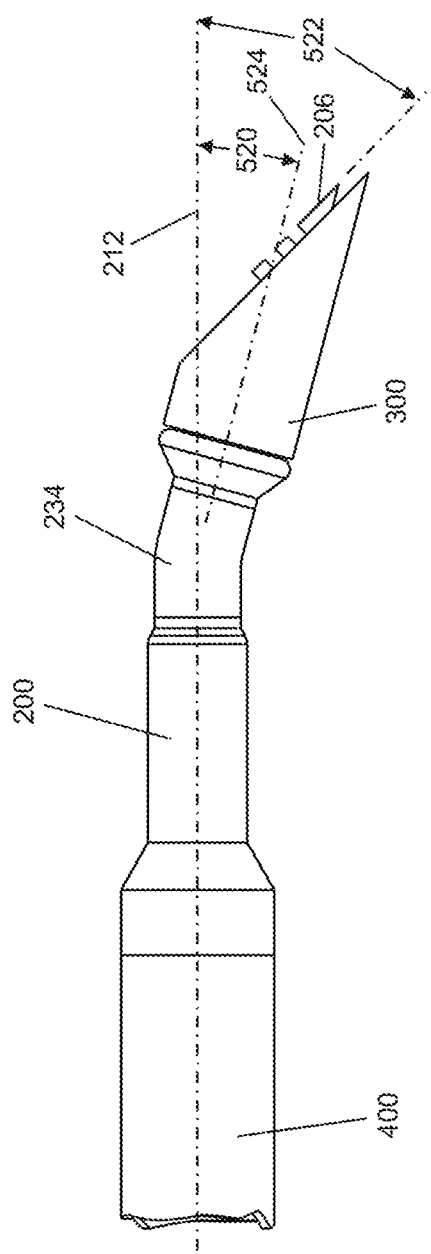
FIG. 24 is a side elevational view of the objects of FIG. 16 wherein the electrode piece has been bent downward to a predetermined angle.
Figure 29:
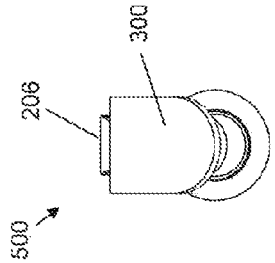
FIG. 29 is an axial elevational view of the objects of FIG. 23.
Figure 26:
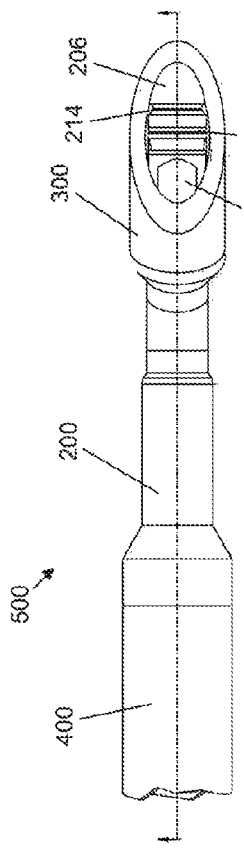
FIG. 26 is a plan view of the objects of FIG. 16 in which the electrode piece has been bent upward to a predetermined angle.
Figure 27:
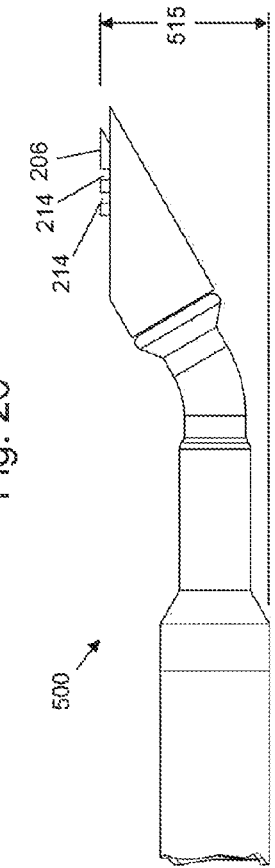
FIG. 27 is a side elevational view of the objects of FIG. 23.

Active element 200 may be bent or flexed as needed. For example, active element 200 may be bent downward, to thereby decrease the angle between the axis of the device and the ablating surface. As depicted in FIGS. 24 and 25, when active element 200 is bent downward, axis 524 of the distal portion of assembly 500 forms angle 520 with axis 212 of tubular member 400, the bend being localized in portion 224 of element 200. Ablating surface 206 forms angle 522 with axis 212 of tubular member 400, said angle typically being on the order of 30 to 80, more preferably 40 to 70. Bent assembly 500 has an overall height of 515, said height typically being on the order of 3 mm (0.12 inches) to 8 mm (0.32 inches), more preferably 3 mm (0.12 inches) to 6 mm (0.24 inches).

Figure 28:
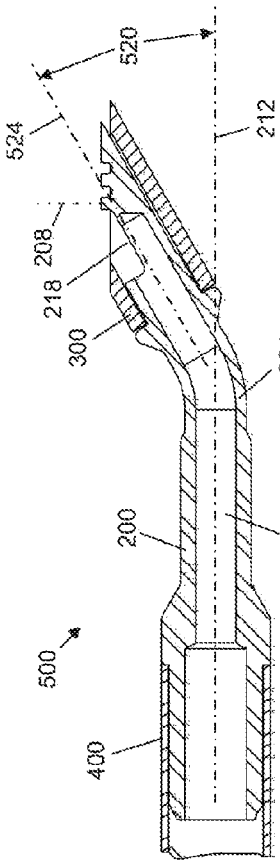
FIG. 28 is a sectional view of the objects of FIG. 23 at location A-A of FIG. 23.

Active element 200 may also be bent upward, to increase the angle between the ablating surface and the axis of the elongate tubular member. FIGS. 26 through 29 depict distal portion 500 in which region 224 of active element 200 has been bent upward, whereby the axis 524 of distal portion 204 of active element 200 forms angle 520 with axis 212 of the proximal portion of element 200 and tubular element 400. Angle 520 is the complement of angle 210 (FIG. 13) between line 208 normal to ablating surface 206 and axis 212. As depicted in FIG. 28, normal line 208 may be made perpendicular to axis 212 to convert distal portion 500 into a "90 degree" ablator. Assembly 500, when formed as shown if FIGS. 26 through 29, has an overall height 515.

It will be understood that, as shown in the figures, singly constructed active element 200 may be flexed to a variety of angled positions, characterized by a range of angles formed between the ablating surface and the axis of the tubular portion, so as to permit introduction of assembly 500 into a wide variety of environments and facilitate application to a wide variety of tissues. Because the bend is concentrated in region 224 of electrode element 200, the overall height 515 is small regardless of the bend. In this manner, the angle will not interfere with or unduly restrict device insertion and manipulation.

During use, RF energy is supplied via tubular element 400 to electrode element 200 to ablating surface 206, which in turn heats the conductive liquid adjacent to and surrounding surface 206. Heating of the liquid continues until boiling of the liquid occurs at surface 206, the boiling occurring first around the edges. Bubbles formed at the surface by the boiling grow until they reach a critical size at which arcing through the bubbles occurs. If ablating surface 206 is brought sufficiently close to the tissue, some of the bubbles will intersect the surface of the tissue, and arcing within these bubbles will pass from the ablating surface 206 to the tissue, each arc vaporizing a discreet volume of tissue. Bubbles and debris created by the tissue vaporization process may then be aspirated from the site.

Figure 30:
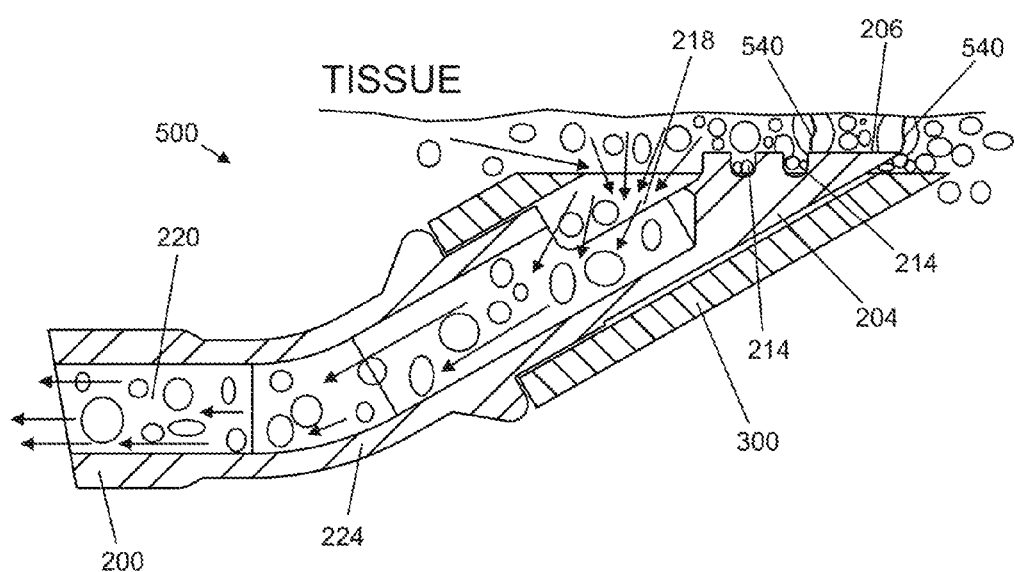
FIG. 30 is a sectional view of the distal portion of the device during use.
Figure 36:
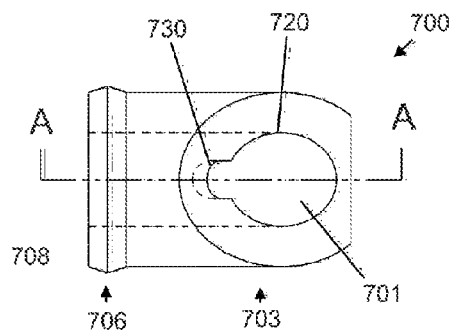
FIG. 36 is a plan view of an insulator for an alternate embodiment of this invention.
Figure 37:
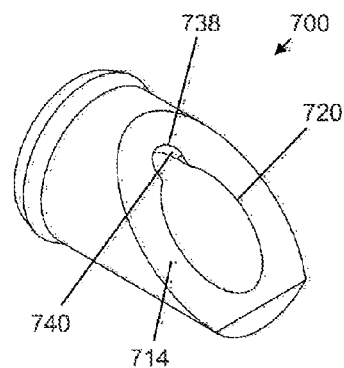
FIG. 37 is a perspective view of the objects of FIG. 36.
Figure 38:
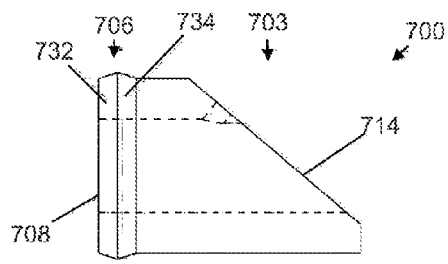
FIG. 38 is a side elevational view of the objects of FIG. 36.
Figure 39:
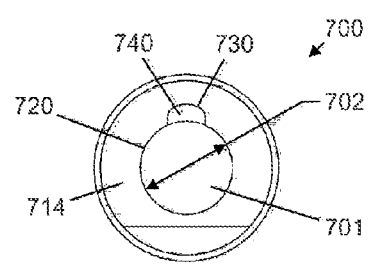
FIG. 39 is a distal axial view of the objects of FIG. 36.
Figure 40:
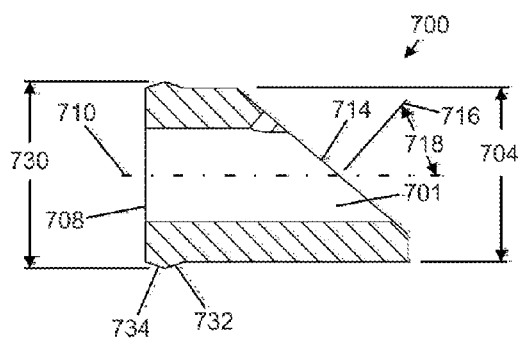
FIG. 40 is a side elevational sectional view of the objects of FIG. 36 at location A-A of FIG. 36.
Figure 41:
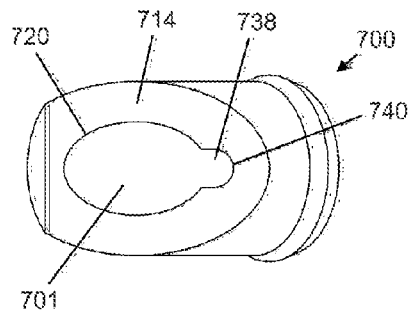
FIG. 41 is a view of the objects of FIG. 36 in direction A-A of FIG. 36.
Figure 42:
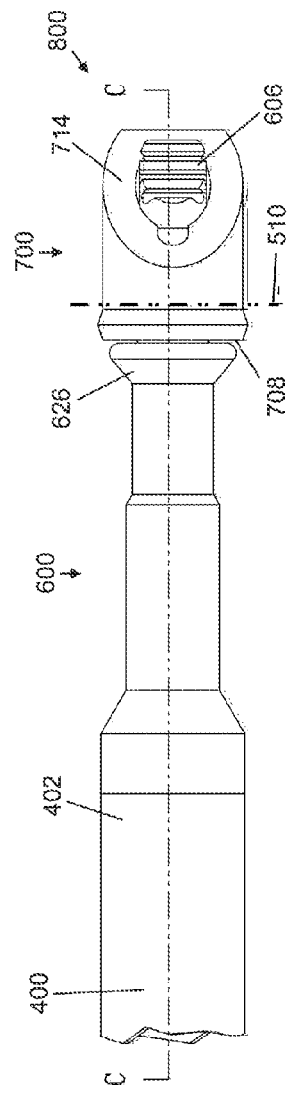
FIG. 42 is a plan view of the distal assembly of an alternate embodiment of the invention herein disclosed.
Figure 43:
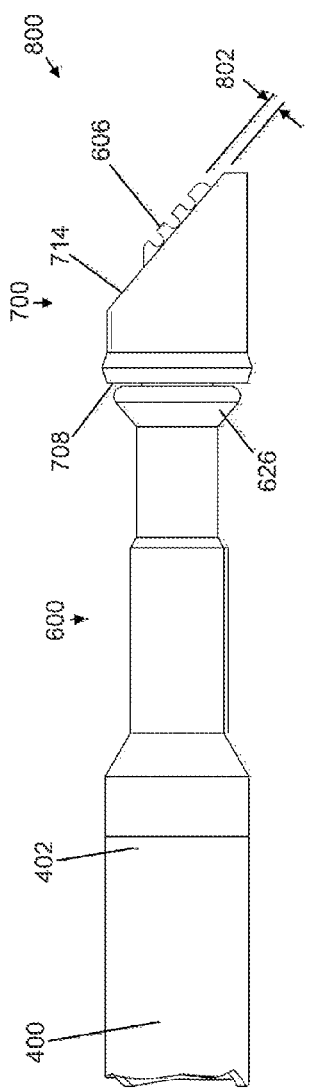
FIG. 43 is a side elevational view of the objects of FIG. 42.
Figure 44:
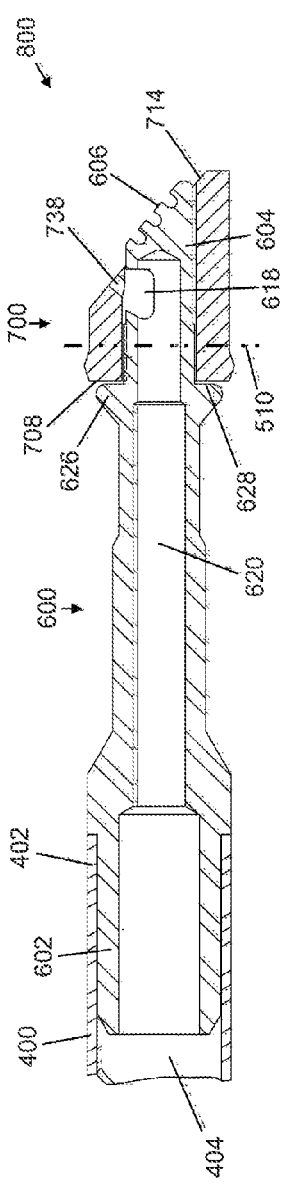
FIG. 44 is a side elevational sectional view of the objects of FIG. 42 at location C-C of FIG. 42.
Figure 46:
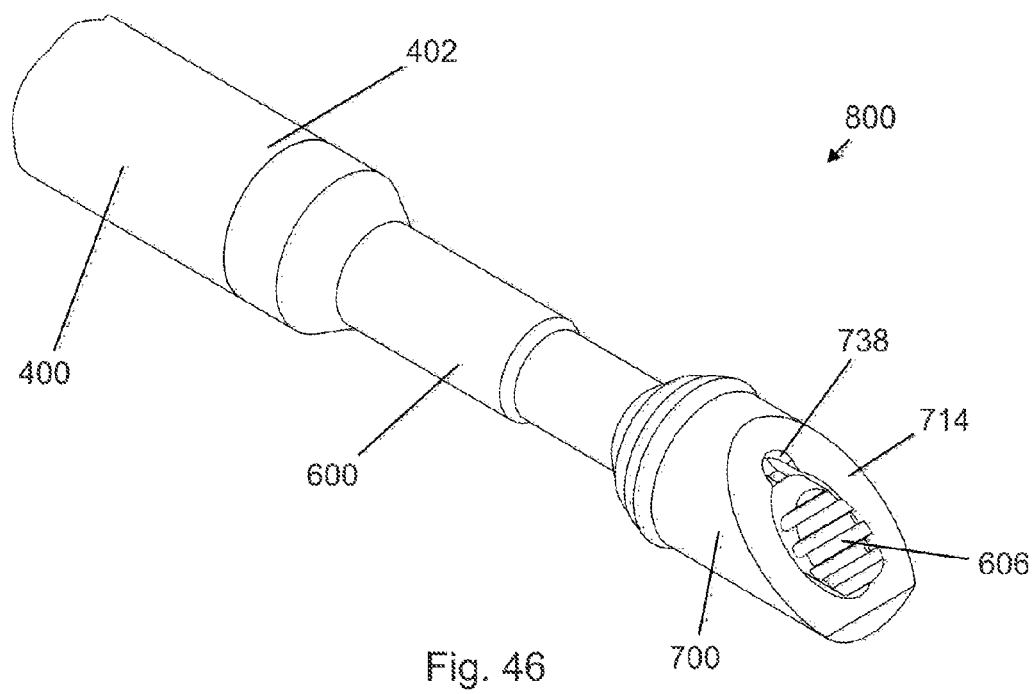
FIG. 46 is a perspective view of the objects of FIG. 42.
Figure 45:
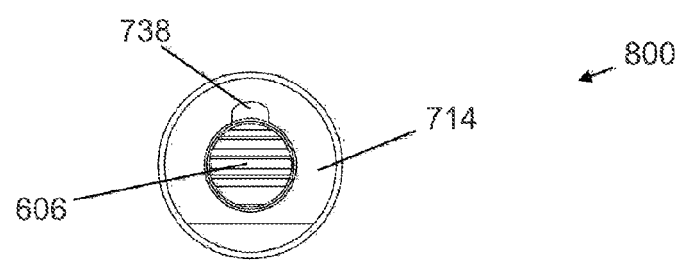
FIG. 45 is a distal axial view of the objects of FIG. 42.
Figure 47:
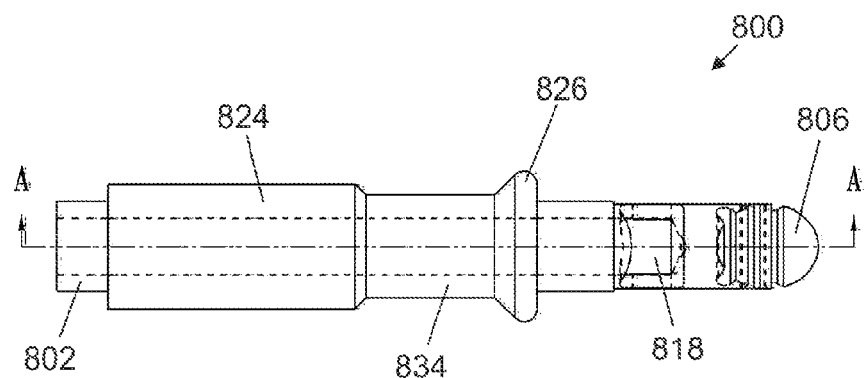
FIG. 47 depicts a plan view of an electrode piece of an alternate embodiment formed in accordance with the principles of this invention.
Figure 48:
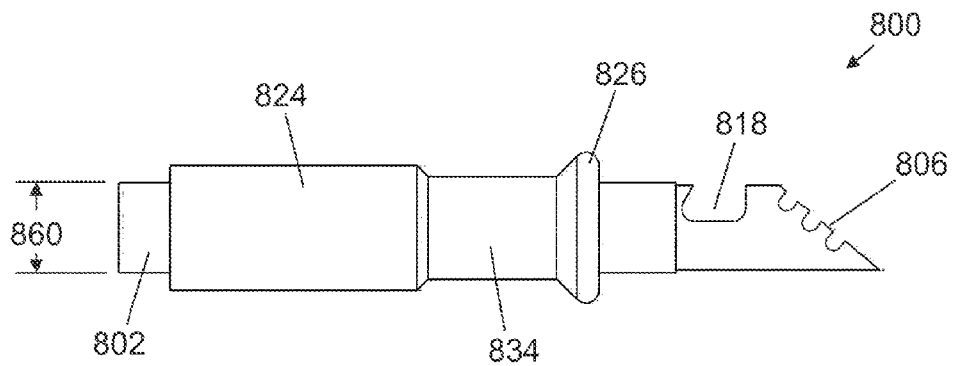
FIG. 48 is a side elevational view of the elements of FIG. 47
Figure 49:
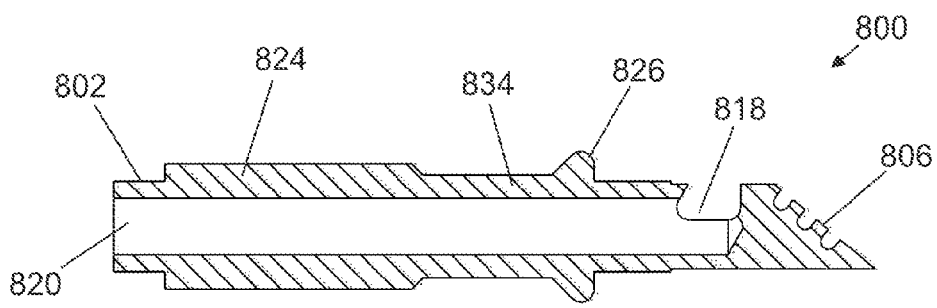
FIG. 49 is a side elevational sectional view of the elements of FIG. 47 at location A-A of FIG. 47.
Figure 50:
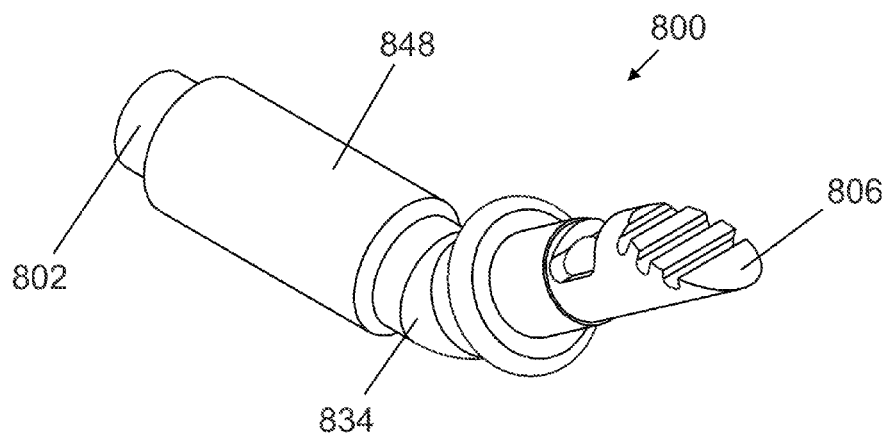
FIG. 50 is a perspective view of the electrode piece of FIG. 47 formed upward to create a 90-degree tip.
Figure 51:
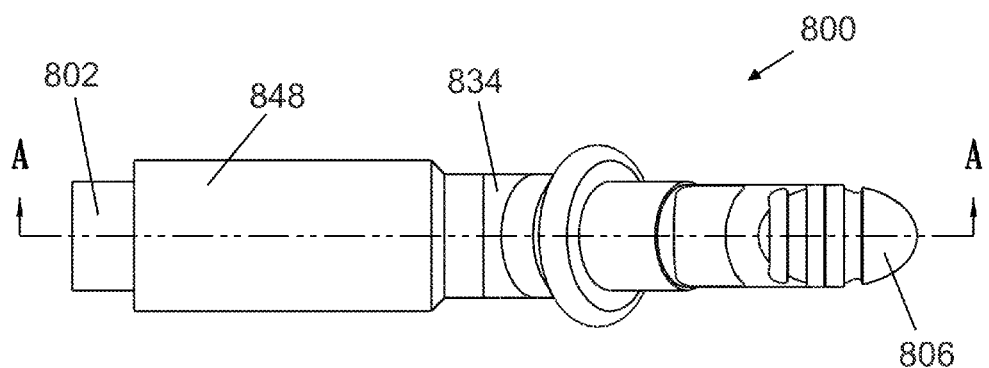
FIG. 51 is a plan of a view of the objects of FIG. 50.
Figure 52:
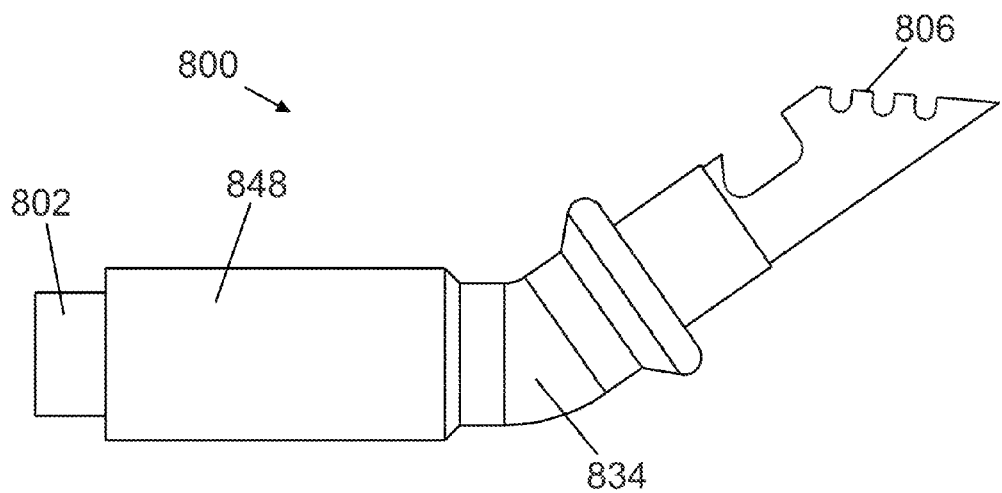
FIG. 52 is a side elevational view of the objects of FIG. 50.
Figure 53:
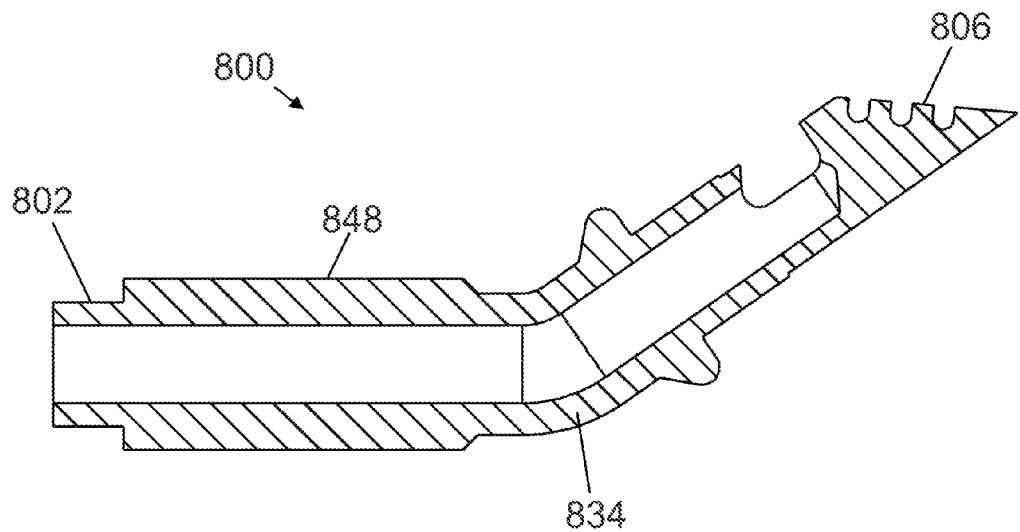
FIG. 53 is a side elevational sectional view at location A-A of FIG. 51.

FIG. 30 depicts this ablation process using assembly 500 formed as shown in FIGS. 26 through 29. Arcs 540 between ablating surface 206 and the tissue vaporize tissue. The ablation by-products and bubbles are removed by the aspiration path provided by aperture 218 and lumen 220 of electrode element 200 and lumen 404 of tubular element 400. Because the aperture 218 is proximally adjacent to the ablating surface 206 but not does not pass directly through surface 206 or intersect grooves 214 in the ablating surface, the amount of process heat removed is minimized. In this manner, aspiration does not interfere with or significantly decrease the efficiency of the ablating process.

An alternate embodiment of a distal end active element for an electrosurgical ablator formed in accordance with the principles of this invention is depicted in FIGS. 31 through 35. Active element 600 is identical in form and function to active element 200 except for the placement and configuration of opening 618 compared to opening 218 of active element 200. Proximal end 602 of active element 600 is configured for mounting to the distal end of a standard electrosurgical shaft or tube. Distal end 604 has an ablating surface 606 formed thereon, wherein a line 608 normal to surface 606 forms an angle 610 with axis 612 of active element 600. Surface 606 has grooves or contours 614 formed or machined therein. Just proximal to surface 606, a lateral opening—aspiration port 618—is disposed, said opening stemming from central lumen 620 of element 600. Proximal to opening 618 is tubular active element portion 619 having an external diameter of 621. Continuing in the proximal direction, one finds middle portion 624 of element 600, a portion having at its distal end flange 626 having a distal surface 628 perpendicular to axis 612, a conical proximal surface 630, and a radiused edge 632 disposed between distal and proximal surfaces. Proximal to flange 626 in middle portion 624 is cylindrical portion 634 of diameter 636 and extending distance 638. The proximal end 640 of middle portion 624 has formed thereon a flange 642 having a proximal planar surface 644 to which axis 612 is normal, and a conical distal surface 646. Distal to distal surface 646, cylindrical portion 648 of diameter 650 extends distally to cylindrical portion 634. Diameter 650 of cylindrical portion 648 is larger than diameter 636 of portion 634.

FIGS. 36 through 41 depict an insulator suitable for use in connection with an alternate embodiment of the present invention. Insulator 700, formed from a suitable dielectric material such as, for instance, alumina, is tubular in form, has a lumen 701 with a diameter 702 sized to be slightly larger than diameter 621 of portion 619 of element 600, and a distal portion 703 with an outside diameter 704. The proximal portion 706 of insulator is characterized by a planar proximal face 708 having a normal parallel to axis 710 of insulator 700. Proximal portion 706 has a maximum diameter 730, which is greater than diameter 704 of distal portion 703, and angled distal and proximal surfaces 732 and 734 respectively. Distal portion 703 has a distal end planar surface 714 having a normal 716 angularly displaced from axis 710 angle 718, angle 718 being approximately equal to angle 610 of element 600. Lumen 701 intersects surface 714 to form distal opening 720. At the proximal end of opening 720, recess 738 is formed, recess 738 having a proximal wall 740.

FIGS. 42 through 46 depict the distal end assembly 800 of an electrosurgical ablator constructed in accordance with the principles of this invention. Proximal end 602 of active element 600 is mounted to the distal end 402 of tube 400. Insulator 700 is mounted to distal end 604 of active element 600, with proximal face 708 of insulator 700 positioned to be adjacent to distal face 628 of flange 626. Distal face 714 of insulator 700 is parallel to ablating surface 606 and is displaced from ablating surface 606 distance 802. Recess 738, opening 618 and lumen 620 of element 600, and lumen 404 of tubular member 400 together provide an aspiration path between the region distal to distal surface 714 and a vacuum source connected via means within the handle to lumen 404 of tubular member 400. A dielectric coating covers assembly 500 and tubular member 400 proximal to line 510.

In some cases, it may be advantageous to minimize the diameter of tube 400, for instance, so that the distal electrode assembly can be incorporated into an ablator having a return electrode on the device. This may be accomplished through elimination of flange 242 (FIGS. 8 through 12) or flange 642 (FIGS. 31 through 34). An alternate embodiment incorporating this configuration is depicted in FIGS. 47 through 57. Active element 800 is identical to active element 600 (depicted in FIGS. 31 through 35) and functions in identical manner, with the exception that flange 642 has been eliminated. Proximal end 802 of active element 800 has a reduced diameter such that proximal end 802 may be inserted into distal end 402 of tube 400. Referring now to FIGS. 51 through 54 depicting an active element 800 that may mounted to distal end 402 of tube 400, proximal end 802 of active element 800 may be affixed to distal end 402 of tube 400 by any suitable means, preferably by welding, more preferably by laser welding. Active element 800 functions in the same manner as previous embodiments in that it is machined or molded in a straight (un-bent) condition and may then be formed (bent) at mid-portion 834 to a range of angles so as to produce more than one product. In the Figures, element 800 is bent to form a 90 degree ablator; however, the invention is not limited thereto and may be readily utilized to produce a variety of products each having a different angle between the tube axis and a normal the ablating surface 806.

INDUSTRIAL APPLICABILITY

The flexible single piece active element of the present invention, as well as the aspirating ablators formed therewith, find utility in the field of bulk tissue vaporization, providing a simple construction suitable for use with a wide array of electrosurgical components and adjustable to wide range of angled positions to permit access to a variety of tissues, in an array of diverse environments and address a host of ablation needs.

Additionally, the novel geometry and positioning of both ablation surface and aspiration port permits aspiration flow to remove primarily waste heat rather than process heat, to thereby improve vaporization efficiency and reduce procedure time. Thus, present invention maximizes efficiency and adaptability while minimizing manufacturing costs and device profile.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. An active electrode for connection to an electrosurgical device for the bulk vaporization of tissue, the electrosurgical device comprising an elongate cannulated tubular member having a proximal end, a distal end and a tubular lumen extending therebetween, wherein said active electrode comprises an open proximal end, a closed distal end and a tubular lumen extending therebetween and further comprises the following features:
   a) a cylindrical distal portion characterized by a longitudinal axis, an outer diameter, and a first tubular lumen section, wherein said cylindrical distal portion comprises (i) a beveled distal-most ablation surface that forms an acute angle with the longitudinal axis of said distal portion and (ii) a lateral opening formed in a side wall of said cylindrical distal portion and positioned proximally to said beveled distal-most ablation surface, said opening extending through the side wall of said cylindrical distal portion into the first tubular lumen section of said active electrode;
   b) a cylindrical middle portion characterized by a longitudinal axis, an outer diameter, and a second tubular lumen section, wherein said cylindrical middle portion is positioned proximally to said cylindrical distal portion, further wherein said cylindrical middle portion and said cylindrical distal portion are not coaxial, further wherein the longitudinal axis of the cylindrical middle portion forms a pre-determined acute angle with the longitudinal axis of said cylindrical distal portion;
   c) a cylindrical proximal portion characterized by a longitudinal axis, an outer diameter, and a third tubular lumen section, wherein said cylindrical proximal portion is positioned proximally adjacent to said cylindrical middle portion, further wherein said cylindrical proximal portion is configured for attachment to the distal end of said elongate cannulated tubular member of said electrosurgical device, further wherein the first, second and third tubular lumen sections comprise the tubular lumen of said active electrode that coordinates with the tubular lumen of said elongate cannulated tubular member to form a continuous aspiration path, thereby allowing the flow of vaporization by-products from the region adjacent to the beveled distal-most ablation surface and to the proximal end of the elongate cannulated tubular member of said electrosurgical device.

2. The active electrode of claim 1, further comprising a raised flange portion disposed between said cylindrical distal portion and said cylindrical middle portion, wherein said flange portion has an outer diameter greater than the outer diameter of said cylindrical distal portion, wherein said flange portion further comprises a distal-facing surface that projects in a direction transverse to the longitudinal axis of said cylindrical distal portion so as to serve as an insulator stop.

3. The active electrode of claim 1, wherein the proximal end of said cylindrical proximal portion has a reduced diameter that facilitates insertion of the proximal end of said active electrode into the distal end of the elongate cannulated tubular member of said electrosurgical device.

4. The active electrode of claim 1 wherein said active electrode components (a)-(c) are molded from a metallic material as a single, continuous, homogeneous element.

5. The active electrode of claim 4 wherein the pre-determined acute angle between said cylindrical distal portion and said cylindrical middle portion of said active electrode is introduced during the molding process.

6. The active electrode of claim 4 wherein the pre-determined acute angle between said cylindrical distal portion and said cylindrical middle portion of said active electrode is introduced after the molding process.

7. The active electrode of claim 1 wherein said active electrode components (a)-(c) are fused into a single unitary element.

8. The active electrode of claim 7, wherein the pre-determined acute angle between said cylindrical distal portion and said cylindrical middle portion of said active electrode is introduced during the fusion process.

9. The active electrode of claim 1, wherein said lateral opening is immediately adjacent to said beveled distal-most surface.

10. The active electrode of claim 1, wherein said lateral opening is displaced proximally a predetermined distance from the beveled distal-most ablation surface.

11. The active electrode of claim 1, wherein the beveled distal-most ablation surface is configured with machined contours.

12. The active electrode of claim 11, wherein said machined contours comprise a series of parallel grooves.

13. The active electrode of claim 11, wherein said machined contours comprise an array of protruding pins.

14. The active electrode of claim 11, wherein said machined contours comprise an array of raised ribs.

15. An electrosurgical assembly for the bulk vaporization of tissue comprising:
   a) an electrosurgical device comprising an elongate cannulated tubular element having a proximal end, a distal end and a tubular lumen extending therebetween; and
   b) the active electrode of claim 1 affixed to the distal end of said elongate cannulated tubular element such that the tubular lumens of said active electrode and said elongate cannulated tubular element coordinate to form a continuous aspiration path allowing the flow of vaporization by-products from the region adjacent to the beveled distal-most ablation surface and to the proximal end of said elongate cannulated tubular element.

16. The electrosurgical assembly of claim 15 wherein said active electrode is affixed to the distal end of said elongate cannulated tubular element by welding.

17. The electrosurgical assembly of claim 15 wherein said active electrode is affixed to the distal end of said elongate cannulated tubular element by laser welding.

18. The electrosurgical assembly of claim 15, wherein active electrode components (a)-(c) are machined or molded in a linear, un-bent configuration and then subsequently bent at the intersection between cylindrical distal and middle portions.

19. A method for forming the active electrode of claim 1, said method comprising the steps of:
   (a) on a screw-machine, lathe or other suitable turning machine, forming a metal blank having (i) cylindrical distal portion of a predetermined length and outer diameter, (ii) a raised flange portion having an outer diameter greater than the outer diameter of said cylindrical distal portion and having a distal-facing surface that projects in a direction transverse to the length of said tubular distal portion so as to serve as an insulator stop, said flange portion being proximally adjacent to said cylindrical distal portion, (iii) a cylindrical middle portion proximal to said flange portion, (iv) a cylindrical proximal-most portion formed for attachment to an elongated cannulated tubular member of an electrosurgical device for the bulk vaporization of tissue, and (v) a central lumen extending from the proximal end of said active electrode to a predetermined depth;
   (b) beveling the distal end of said blank to form an angled distal most surface on said blank;
   (c) forming a lateral opening between the exterior surface of said cylindrical distal portion and the central lumen; and
   (d) bending the tubular middle portion a pre-determined acute angle such that cylindrical distal portion and said cylindrical middle portion are not coaxial to thereby give rise to the active electrode as set forth in claim 1.

20. The active electrode of claim 2, wherein said flange portion distal-facing surface is flat.

\* \* \* \* \*